(12) United States Patent
Kopperdahl et al.

(10) Patent No.: US 9,848,818 B1
(45) Date of Patent: Dec. 26, 2017

(54) CLINICAL ASSESSMENT OF FRAGILE BONE STRENGTH

(71) Applicant: O.N.Diagnostics, LLC, Berkeley, CA (US)

(72) Inventors: David L. Kopperdahl, Berkeley, CA (US); Paul Frederick Hoffmann, Oakland, CA (US); David Choen Lee, Arcadia, CA (US); Garry Thomas Hayeck, Lower Gwynedd, PA (US); Tony M. Keaveny, Berkeley, CA (US)

(73) Assignee: O.N.Diagnostics, LLC, Berkeley, CA (US)

( * ) Notice: Subject to any disclaimer, the term of this patent is extended or adjusted under 35 U.S.C. 154(b) by 340 days.

(21) Appl. No.: 14/455,867

(22) Filed: Aug. 8, 2014

Related U.S. Application Data

(60) Provisional application No. 61/864,458, filed on Aug. 9, 2013.

(51) Int. Cl.
| | |
|---|---|
| *A61B 5/05* | (2006.01) |
| *A61B 5/00* | (2006.01) |
| *A61B 5/055* | (2006.01) |
| *A61B 6/03* | (2006.01) |
| *A61B 6/00* | (2006.01) |
| *A61B 8/08* | (2006.01) |

(52) U.S. Cl.
CPC ............ *A61B 5/4509* (2013.01); *A61B 5/055* (2013.01); *A61B 5/7246* (2013.01); *A61B 6/032* (2013.01); *A61B 6/505* (2013.01); *A61B 6/5211* (2013.01); *A61B 8/0875* (2013.01); *A61B 8/5215* (2013.01)

(58) Field of Classification Search
CPC ....... A61B 5/4509; A61B 5/055; A61B 6/032; A61B 6/5211; A61B 8/0875; A61B 5/7246; A61B 8/5215; A61B 6/505
USPC .......................... 600/407–480; 382/128–132
See application file for complete search history.

(56) References Cited

U.S. PATENT DOCUMENTS

| | | | |
|---|---|---|---|
| 4,721,112 A | 1/1988 | Hirano et al. | |
| 5,172,695 A | * 12/1992 | Cann ................... | G06F 19/3437 378/54 |
| 6,246,745 B1 | 6/2001 | Bi et al. | |
| 6,249,692 B1 | 6/2001 | Cowin | |
| 6,442,287 B1 | 8/2002 | Jiang et al. | |
| 6,853,741 B1 * | 2/2005 | Ruth ..................... | G06T 7/0012 382/132 |
| 6,975,894 B2 | 12/2005 | Wehrli et al. | |
| 7,124,067 B2 | 10/2006 | Ascenzi | |
| 7,353,153 B2 | 4/2008 | Ascenzi et al. | |
| 7,424,142 B2 | 9/2008 | Arnold | |

(Continued)

OTHER PUBLICATIONS

Bousson, V., C. Bergot, B. Sutter, P. Levitz, B. Cortet and O. Scientific Committee of the Groupe de Recherche et d'Information sur les (2012). "Trabecular bone score (TBS): available knowledge, clinical relevance, and future prospects." Osteoporos Int 23(5): 1489-1501.

(Continued)

*Primary Examiner* — Sanjay Cattungal
(74) *Attorney, Agent, or Firm* — Patent Law Offices Michael E. Woods; Michael E. Woods

(57) ABSTRACT

A system and method for the use of the results from a structural analysis of a patient's bone from a clinical scan, to be used clinically to manage patients in a widespread and consistent fashion.

9 Claims, 12 Drawing Sheets

(56) References Cited

U.S. PATENT DOCUMENTS

| | | |
|---|---|---|
| 7,769,214 B2 | 8/2010 | Wehrli et al. |
| 7,822,253 B2 | 10/2010 | Joshi et al. |
| 7,840,247 B2 | 11/2010 | Liew et al. |
| 8,073,521 B2 | 12/2011 | Liew et al. |
| 8,290,564 B2 | 10/2012 | Lang et al. |
| 8,480,679 B2 | 7/2013 | Park et al. |
| 8,880,143 B2* | 11/2014 | Kalvesten ............ G06T 7/0014 378/54 |
| 2003/0112921 A1* | 6/2003 | Lang ...................... A61B 6/505 378/54 |
| 2003/0194057 A1 | 10/2003 | Dewaele |
| 2004/0077088 A1* | 4/2004 | Charles, Jr. ........... A61B 6/032 435/455 |
| 2004/0242987 A1* | 12/2004 | Liew ...................... A61B 6/482 600/407 |
| 2005/0010106 A1* | 1/2005 | Lang ...................... A61B 6/469 600/425 |
| 2005/0148860 A1* | 7/2005 | Liew ...................... A61B 6/505 600/410 |
| 2007/0047794 A1* | 3/2007 | Lang .................... G06T 7/0012 382/132 |
| 2007/0274442 A1* | 11/2007 | Gregory ................ A61B 6/482 378/54 |
| 2008/0058613 A1 | 3/2008 | Lang et al. |
| 2011/0213242 A1 | 9/2011 | Budoff et al. |
| 2011/0301982 A1 | 12/2011 | Green, Jr. et al. |
| 2012/0224758 A1* | 9/2012 | Treece .................. G06T 7/0012 382/131 |
| 2012/0290957 A1 | 11/2012 | Chernilo |
| 2013/0170614 A1* | 7/2013 | Yoshikawa ............ A61B 6/505 378/56 |
| 2013/0184556 A1* | 7/2013 | Kalvesten ............. A61B 6/505 600/407 |
| 2013/0204595 A1 | 8/2013 | Keyak |
| 2013/0272594 A1* | 10/2013 | Zelzer .................. G06T 3/0043 382/131 |
| 2014/0376701 A1 | 12/2014 | Kopperdahl et al. |

OTHER PUBLICATIONS

Bousson, V. D., J. Adams, K. Engelke, M. Aout, M. Cohen-Solal, C. Bergot, D. Haguenauer, D. Goldberg, K. Champion, R. Aksouh, E. Vicaut and J. D. Laredo (2011). "In vivo discrimination of hip fracture with quantitative computed tomography: results from the prospective European Femur Fracture Study (EFFECT)." J Bone Miner Res 26(4): 881-893.

Bredbenner, T. L., R. L. Mason, L. M. Havill, E. S. Orwoll and D. P. Nicolella (2012). Investigating fracture risk classifiers based on statistical shape and density modeling and the MrOS data set. Orthopaedic Research Society, San Francisco, CA, USA, Trans. Ortho. Res. Soc.

Burghardt, A. J., T. M. Link and S. Majumdar (2011). "High-resolution computed tomography for clinical imaging of bone microarchitecture." Clin Orthop Relat Res 469(8): 2179-2193.

Carballido-Gamio, J., R. Harnish, I. Saeed, T. Streeper, S. Sigurdsson, S. Amin, E. J. Atkinson, T. M. Therneau, K. Siggeirsdottir, X. Cheng, L. J. Melton, 3rd, J. Keyak, V. Gudnason, S. Khosla, T. B. Harris and T. F. Lang (2013). "Proximal femoral density distribution and structure in relation to age and hip fracture risk in women." J Bone Miner Res 28(3): 537-546.

Cody, D. D., G. J. Gross, F. J. Hou, H. J. Spencer, S. A. Goldstein and D. P. Fyhrie (1999). "Femoral strength is better predicted by finite element models than QCT and DXA." J Biomech 32(10): 1013-1020.

Crawford, R. P., C. E. Cann and T. M. Keaveny (2003). "Finite element models predict in vitro vertebral body compressive strength better than quantitative computed tomography." Bone 33(4): 744-750.

Danielson, M. E., T. J. Beck, A. S. Karlamangla, G. A. Greendale, E. J. Atkinson, Y. Lian, A. S. Khaled, T. M. Keaveny, D. Kopperdahl, K. Ruppert, S. Greenspan, M. Vuga and J. A. Cauley (2013). "A comparison of DXA and CT based methods for estimating the strength of the femoral neck in post-menopausal women." Osteoporos Int 24(4): 1379-1388.

Engelke, K., J. E. Adams, G. Armbrecht, P. Augat, C. E. Bogado, M. L. Bouxsein, D. Felsenberg, M. Ito, S. Prevrhal, D. B. Hans and E. M. Lewiecki (2008). "Clinical use of quantitative computed tomography and peripheral quantitative computed tomography in the management of osteoporosis in adults: the 2007 ISCD Official Positions." J Clin Densitom 11(1): 123-162.

Engelke, K., C. Libanati, T. Fuerst, P. Zysset and H. K. Genant (2013). "Advanced CT based In Vivo Methods for the Assessment of Bone Density, Structure, and Strength." Curr Osteoporos Rep 11(3): 246-255.

Faulkner, K. G., C. E. Cann and B. H. Hasegawa (1991). "Effect of bone distribution on vertebral strength: assessment with patient-specific nonlinear finite element analysis." Radiology 179(3): 669-674.

Grimal, Q., J. Grondin, S. Guerard, R. Barkmann, K. Engelke, C. C. Gluer and P. Laugier (2013). "Quantitative ultrasound of cortical bone in the femoral neck predicts femur strength: results of a pilot study." J Bone Miner Res 28(2): 302-312.

Kazakia, G. J., B. Hyun, A. J. Burghardt, R. Krug, D. C. Newitt, A. E. de Papp, T. M. Link and S. Majumdar (2008). "In vivo determination of bone structure in postmenopausal women: a comparison of HR-pQCT and high-field MR imaging." J Bone Miner Res 23(4): 463-474.

Kazakia, G. J. and S. Majumdar (2006). "New imaging technologies in the diagnosis of osteoporosis." Rev Endocr Metab Disord 7(1-2): 67-74.

Keaveny, T. M. (2010). "Biomechanical computed tomography-noninvasive bone strength analysis using clinical computed tomography scans." Ann N Y Acad Sci 1192: 57-65.

Keaveny, T. M., D. L. Kopperdahl, L. J. Melton, 3rd, P. F. Hoffmann, S. Amin, B. L. Riggs and S. Khosla (2010). "Age-dependence of femoral strength in white women and men." J Bone Miner Res 25(5): 994-1001.

Keaveny, T. M., M. R. McClung, H. K. Genant, J. R. Zanchetta, D. Kendler, J. P. Brown, S. Goemaere, C. Recknor, M. L. Brandi, R. Eastell, D. L. Kopperdahl, K. Engelke, T. Fuerst, H. S. Radcliffe and C. Libanati (2014). "Femoral and vertebral strength improvements in postmenopausal women with osteoporosis treated with denosumab." J Bone Miner Res 29(1): 158-165.

Keyak, J. H. (2000). "Relationships between femoral fracture loads for two load configurations." J Biomech 33(4): 499-502.

Keyak J. H., S. A. Rossi, K. A. Jones and H. B. Skinner (1998). "Prediction of femoral fracture load using automated finite element modeling." J Biomech 31(2): 125-133.

Keyak, J. H., S. Sigurdsson, G. Karlsdottir, D. Oskarsdottir, A. Sigmarsdottir, S. Zhao, J. Kornak, T. B. Harris, G. Sigurdsson, B. Y. Jonsson, K. Siggeirsdottir, G. Eiriksdottir, V. Gudnason and T. F. Lang (2011). "Male-female differences in the association between incident hip fracture and proximal femoral strength: a finite element analysis study." Bone 48(6): 1239-1245.

Khoo, B. C., K. Brown, C. Cann, K. Zhu, S. Henzell, V. Low, S. Gustafsson, R. I. Price and R. L. Prince (2009). "Comparison of QCT-derived and DXA-derived areal bone mineral density and T scores." Osteoporos Int 20(9): 1539-1545.

Nicolella, D. P. and T. L Bredbenner (2012). "Development of a parametric finite element model of the proximal femur using statistical shape and density modelling." Comput Methods Biomech Biomed Engin 15(2): 101-110.

Pothuaud, L., P. Carceller and D. Hans (2008). "Correlations between grey-level variations in 2D projection images (TBS) and 3D microarchitecture: applications in the study of human trabecular bone microarchitecture." Bone 42(4): 175-787.

Ulrich, D., B. van Rietbergen, A. Laib and P. Ruegsegger (1999). "The ability of three-dimensional structural indices to reflect mechanical aspects of trabecular bone." Bone 25(1): 55-60.

(56) References Cited

OTHER PUBLICATIONS

Wang, X., A. Sanyal, P. M. Cawthon, L. Palermo, M. Jekir, J. Christensen, K. E. Ensrud, S. R. Cummings, E. Orwoll, D. M. Black and T. M. Keaveny (2012). "Prediction of new clinical vertebral fractures in elderly men using finite element analysis of CT scans." J Bone Miner Res 27(4): 808-816.

Wehrli, F. W., B. R. Gomberg, P. K. Saha, H. K. Song, S. N. Hwang and P. J. Snyder (2001). "Digital topological analysis of in vivo magnetic resonance microimages of trabecular bone reveals structural implications of osteoporosis." J Bone Miner Res 16(8): 1520-1531.

Yang, L., N. Peel, J. A. Clowes, E. V. McCloskey and R. Eastell (2009). "Use of DXA-based structural engineering models of the proximal femur to discriminate hip fracture." J Bone Miner Res 24(1): 33-42.

Yoshikawa, T., C. H. Turner, M. Peacock, C. W. Slemenda, C. M. Weaver, D. Teegarden, P. Markwardt and D. B. Burr (1994). "Geometric structure of the femoral neck measured using dual-energy x-ray absorptiometry [published erratum appears in Journal of Bone and Mineral Research Mar. 1995;10(3):510]." J Bone Miner Res 9(7): 1053-1064.

Zysset, P. K., E. Dall'ara, P. Varga and D. H. Pahr (2013). "Finite element analysis for prediction of bone strength." Bonekey Rep 2: 386.

\* cited by examiner

CLINICAL ASSESSMENT OF FRAGILE BONE STRENGTH

CROSS REFERENCE TO RELATED APPLICATIONS

This application claims benefit of U.S. Patent Application No. 61/864,458, the contents of which are hereby expressly incorporated in its entirety for all purposes.

FIELD OF THE INVENTION

The present invention relates generally to diagnosis of osteoporosis and assessment of fracture risk in live patients by analysis of a medical image.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Osteoporosis is a major public health threat for over 50% of the U.S. population over age 50—an estimated 44 million American women and men—and with the growing size of the elderly population, the need for improved diagnosis and monitoring of drug treatments continues to increase. About 10 million Americans are estimated to already have the disease, the other 34 million with low bone mass (or "osteopenia") are at increased risk for osteoporosis. The most serious complication of osteoporosis is a fractured bone, particularly at the hip. Other types of osteoporotic fractures include spine fractures, the most common type of osteoporotic fracture, and also fractures of the wrist, humerus, ribs, and other smaller bones. One problem in clinically managing osteoporosis is that too few women and men are identified with this disease, and therefore too few are placed on the widely available therapeutic treatments that are known to reduce fracture incidence. As a result of this under-testing, there is a need for additional types of clinical tests that can be implemented in a consistent and widespread manner and that are effective at identifying patients at high risk of an osteoporotic fracture.

The current clinical standard test for identifying people at high risk of osteoporotic fracture is the dual energy X-ray absorptiometry test (more often referred to as DEXA or DXA). The main outcome of the DXA test is a measure of bone mineral density (BMD, in units of $g/cm^2$). To facilitate comparison of BMD values for different types of DXA machines, the BMD value from a DXA test is usually reported as a "T-score", defined as how much the patient's BMD is below the average BMD of a young reference population, expressed in terms of standard deviations of BMD for that reference population. So, for example, if a patient has a T-score of −1.2, it indicates that the patient's BMD is 1.2 standard deviations below the average BMD in the young reference population. The most widely adopted clinical definition of osteoporosis is a BMD T-score of −2.5 or lower, with another condition, known as "osteopenia" or "low bone mass", defined as when the BMD T-score is between −2.5 and −1.0; "normal" BMD is when the T-score is −1.0 or higher. The BMD can be measured at the hip or spine, and usually if the T-score from any of these sites is −2.5 or lower, the patient is said to have osteoporosis; if all T-scores are greater than −2.5 but at least one T-score is between −2.5 and −1.0, then the patient is said to have osteopenia. Another established clinical test is quantitative computed tomography (CT), which provides a measure of BMD (in units of $mg/cm3$) of the vertebral trabecular bone. When this measure of BMD is less than 80 $mg/cm3$, a patient is considered to have osteoporosis. See for example, Engelke (Engelke K, Adams J E, Armbrecht G, Augat P, Bogado C E, Bouxsein M L, Felsenberg D, Ito M, Prevrhal S, Hans D B, Lewiecki E M. Clinical use of quantitative computed tomography and peripheral quantitative computed tomography in the management of osteoporosis in adults: the 2007 ISCD Official Positions. J Clin Densitom. 11:123-62, 2008). Quantitative CT of the hip can also be used to provide a DXA-equivalent BMD at the hip, and the associated T-scores; see for example, Khoo (Khoo (Comparison of QCT-derived and DXA-derived areal bone mineral density and T scores. Khoo B C, Brown K, Cann C, Zhu K, Henzell S, Low V, Gustafsson S, Price R I, Prince R L. Osteoporos Int. 20:1539-45, 2009).

Many fracture-outcome clinical studies have shown that patients who have osteoporosis are indeed at high risk of fracture, and as a result of such findings, a patient with BMD-defined osteoporosis is a good candidate for therapeutic treatment. Indeed, the BMD values that correspond to a definition of osteoporosis have become an almost universally accepted interventional threshold value for the treatment of elderly patients with osteoporosis. That is to say, patients with a BMD score equal to or less than the interventional threshold value for osteoporosis are recommended for some form of therapeutic intervention or treatment. In general, without a well validated and clinically accepted interventional threshold value, the results of any new bone test would be difficult to implement clinically since physicians would otherwise not know how to consistently interpret the results of such a new test in terms of deciding whether or not to recommend that a patient undergo therapeutic treatment.

A second challenge for any new bone tests relates to the clinical finding that about half of osteoporotic hip fractures occur in elderly people who do not have osteoporosis, but who instead only have osteopenia. Thus, there remains a need for new clinical tests that can identify high-risk patients with osteoporosis and also some high-risk patients with osteopenia who are nonetheless at high risk of fracture.

One such potential alternative test to DXA is based on the method of finite element analysis of computed tomography (CT) scans for patient-specific assessment of bone strength, termed here "Biomechanical CT" analysis, or "BCT". See, for example, U.S. Pat. No. 5,172,695 for a description of such finite element analysis of quantitative CT scans for clinical bone strength analysis, which is expressly included herein in its entirety by reference, for all purposes. See also Faulkner et al. (Effect of bone distribution on vertebral strength: assessment with patient-specific nonlinear finite element analysis. Radiology. 179:669-674, 1991), Keyak et al. (Prediction of femoral fracture load using automated finite element modeling. J Biomech. 31:125-133, 1998), Cody et al. (Femoral strength is better predicted by finite element models than QCT and DXA. J Biomech. 32:1013-1020, 1999), Keyak (Relationships between femoral fracture loads for two load configurations. J Biomech. 33:499-502, 2000), Crawford et al. (Finite element models predict in vitro vertebral body compressive strength better than quantitative computed tomography. Bone. 33:744-750, 2003), and Nicolella and Bredbenner (Development of a parametric finite element model of the proximal femur using statistical shape and density modelling. Comput Methods Biomech Biomed Engin. 15:101-10, 2012)—all of which are expressly included herein in their entireties by reference.

In development in academia for over 20 years, the BCT method combines image processing of clinical CT scans, bone biomechanics, and the engineering computational mechanics technique of finite element analysis to provide a "virtual stress test" of a bone. The primary outcome of the test is an estimate of the strength (in units of Newtons) of the whole bone or a portion thereof, for example, a femur, a vertebral body, or a proximal femur. Cadaver studies have shown that the BCT method provides excellent non-invasive estimates of bone strength for the hip and spine and other bones. Clinical fracture-outcome studies have also shown that the estimates of bone strength obtained from the BCT technique are significantly associated with the risk of fracture. Despite its potential and its long history, the BCT technique has remained a niche research tool and has not yet been developed as an effective clinical test that can reliably identify patients at high risk of fracture in clinical practice. Part of the reason for this is the difficulty in establishing a credible and robust interventional threshold value for the BCT-generated values of bone strength that can be confidently adopted by clinicians, and approved by federal regulators.

This same challenge applies to the clinical use of results from any type of bone structural analysis performed on any type of medical image. For example, two-dimensional dual energy X-ray (DXA) scans of a bone can be processed to provide structural measures associated with the strength and structure of the bone, including but not limited to a buckling ratio, a femoral neck diameter, a hip axis length, various different composite bending and compressive strength indices, as well as measures of trabecular microarchitecture, for example as described in Danielson (Danielson M E, Beck T J, Karlamangla A S, Greendale G A, Atkinson E J, Lian Y, Khaled A S, Keaveny T M, Kopperdahl D, Ruppert K, Greenspan S, Vuga M, Cauley J A: A comparison of DXA and CT based methods for estimating the strength of the femoral neck in post-menopausal women. Osteoporos Int, 24:1379-88, 2013) and Pothuaud (Pothuaud L, Carceller P, Hans D: Correlations between grey-level variations in 2D projection images (TBS) and 3D microarchitecture: applications in the study of human trabecular bone microarchitecture. Bone 42:775-87, 2008)—all of which are expressly included herein in their entireties by reference. X-ray images can also be analyzed for bone structure and strength, as described by US patent application U.S. Ser. No. 11/855,939 and U.S. Pat. No. 8,073,521. Magnetic resonance scans, ultrasound scans, and CT scans can also be processed in various ways to provide structural measures associated with the strength and structure of the bone, for example, as described by Burghardt (High-resolution computed tomography for clinical imaging of bone microarchitecture. Burghardt A J, Link T M, Majumdar S. Clin Orthop Relat Res. 469:2179-93, 2011), Wehrli (Wehrli F W, Gomberg B R, Saha P K, Song H K, Hwang S N, Snyder P J: Digital topological analysis of in vivo magnetic resonance micro-images of trabecular bone reveals structural implications of osteoporosis. J Bone Miner Res 16:1520-1531, 2001), Grimal (Quantitative ultrasound of cortical bone in the femoral neck predicts femur strength: results of a pilot study. Grimal Q, Grondin J, Guérard S, Barkmann R, Engelke K, Glüer C C, Laugier P. J Bone Miner Res. 28:302-12, 2013), Kazakia (In vivo determination of bone structure in postmenopausal women: a comparison of HR-pQCT and high-field MR imaging. Kazakia G J, Hyun B, Burghardt A J, Krug R, Newitt D C, de Papp A E, Link T M, Majumdar S. J Bone Miner Res. 23:463-74, 2008), and Bredbenner (Bredbenner T L, Mason R L, Havill L M, Orwoll S, Nicolella D P. Investigating fracture risk classifiers based on statistical shape and density modeling and the MrOS data set. In: Orthopaedic Research Society: Proceedings of the Annual Meeting of the Orthopaedic Research Society: 2012; San Francisco, Calif.)—all of which are expressly included herein in their entireties by reference.

When an interventional threshold value from any type of structural analysis of a bone is used clinically by a physician to decide on the course of action of medical management of a patient, any such interventional threshold value needs to be extensively validated and approved by a regulatory agency (e.g. the Food & Drug Administration in the U.S.). One approach to identifying values of an effective interventional threshold from a structural analysis of a bone is to conduct a series of fracture-outcome clinical studies in order to explore the ability of the new test to identify patients at high risk of fracture, and then on the basis of such studies choose a value of the interventional threshold. This is effectively a calibration process. Then, there is an additional need to prospectively validate this choice of threshold value in a general fashion, which typically requires multiple additional fracture-outcomes studies, independent of the clinical studies conducted in the calibration phase. Overall, this is a very expensive and time enduring developmental process since prospective fracture-outcome studies can take a long time to conduct (5-7 years) and oftentimes can involve many hundreds or thousands of patients. Thus, there is a need to facilitate this overall calibration and validation process so it is less expensive and time-consuming.

In addition, since clinical studies consistently show that compliance—the rates of patients taking their recommended medication—for osteoporosis drug treatment is low, there is also a need in developing any new clinical tests based on a structural analysis of a bone to help patients who are identified at high risk of fracture to better appreciate the extent of their compromised bone strength so that they are better motivated to undergo appropriate medical treatment. This lack of compliance is a major problem in treating osteoporosis since therapies need to be continued for multiple years for sustained protection. Typical medical reports generated from a DXA test consist of an X-ray type of picture of the patient's bone, numerical values of BMD and T-scores, and some charts of such values plotted against age, oftentimes with zones of "osteoporosis" highlighted on the chart. Also, certain "risk calculator" tools are also available that can report an absolute risk of fracture, such as a 5- or 10-year probability of fracture, expressed as a percentage. As a result of the difficulty in interpreting such medical reports and numerical scores, and the sometimes abstract and non-intuitive nature of the information in the report from a patient's perspective, and since osteoporosis is not painful unless there is a bone fracture, many patients who have not yet fractured but who are at high risk of a fracture find it difficult to really understand the outcome of the imaging tests or appreciate the severity of their medical condition. Thus, there is a need for a medical assessment/report that is more intuitive and easy to understand by the typical patient.

BRIEF SUMMARY OF THE INVENTION

Disclosed is a system and method for the use of the results from a non-invasive structural analysis of a patient's bone, or portion thereof, using information from a clinical scan of the patient's bone, to be used clinically to manage patients in a widespread and consistent fashion. In the most general embodiment, as depicted in FIG. 1, the results 20 of a structural analysis of a patient's bone are used, in conjunction with a predetermined interventional threshold value 30, to classify the patient for "fragile-bone-strength" 40, and the results are written to a medical report 50 for use by the physician in managing the patient clinically. In one particular embodiment, using a patient-specific finite element analysis derived from a clinical CT scan of a patient's bone, a patient's bone strength is non-invasively assessed via a computational virtual stress test. Instead of using a patient-specific finite element analysis of a CT scan, various prior art methods for estimating bone strength or a bone structural parameter from any medical image (such as CT, MRI, ultrasound, or DXA), referenced above and incorporated herein, can also be used instead for this step. Then, the patient's bone strength—or other bone structural parameter—is compared to a predetermined interventional threshold value, termed the threshold value for "fragile-bone-strength", defined herein as the level of bone strength that corresponds statistically to the level of bone mineral density (BMD) that clinically defines osteoporosis. Importantly, the interventional threshold value for fragile-bone-strength is specified on the basis of the statistical relation between BMD and bone strength, exploiting the fact that the BMD-based interventional threshold value for osteoporosis is well established and therefore serves as a reference with which to specify the interventional threshold value for fragile-bone-strength. Patients are said to have "fragile-bone-strength" when their bone strength is less than or equal to this interventional threshold value. Results are then written to a medical report or otherwise saved on a computer medium, said report optionally displaying the interventional threshold values for fragile-bone-strength.

This method successfully identifies patients at high risk of fracture who have osteoporosis and also many high-risk patients who do not have osteoporosis but have low bone mass (also known as osteopenia). As noted above, one important feature of this invention is the method of defining the interventional threshold value of fragile-bone-strength based on the BMD-defined interventional threshold level of osteoporosis. Another is the use of measures of both BMD and bone strength, combined, to identify patients at high risk of fracture, enabled by the use of a predetermined value of the interventional threshold for fragile-bone-strength. Such a method is beneficial because it can consistently identify more patients at high risk of fracture than by using just BMD alone, some of these patients having osteopenia. While one embodiment relates to bone strength as estimated by finite element analysis of CT scans, the invention can be used to define an interventional threshold value for any result of any type of bone structural analysis performed on any type of medical image so long as there is a statistical relation between said result and a measure of BMD that is used clinically to define osteoporosis.

One benefit of the invention is that it can reduce the expense and time required to calibrate or specify an interventional threshold value for a result from a bone structural analysis of a patient-specific medical image because it does not require any fracture-outcome study for such purposes.

One additional feature of this invention is the method of determining an assessment and generating a medical report that can be used by patients to better understand their bone status. In one embodiment, a "dynamic" report depicts the virtual stress test used to non-invasively assess the patient's bone strength, and visually displays crushing and/or damage within the patient's own bone if their bone virtually fails when loaded to force levels that are at or below the predetermined interventional threshold value for fragile-bone-strength. In another embodiment, the patient can visualize their bone after various hypothetical situations to help motivate them to seek therapeutic treatment if they have fragile-bone-strength, including a situation of not receiving any treatment or a situation of receiving one of various treatment options. An integral element of these embodiments is the interventional threshold value for fragile-bone-strength.

The following summary of the invention is provided to facilitate an understanding of some of the technical features related to, and the use of, non-invasive assessment of fragile-bone-strength in live patients derived from analysis of a patient's clinical scan, and is not intended to be a full description of the present invention. A full appreciation of the various aspects of the invention can be gained by taking the entire specification, claims, drawings, and abstract as a whole. The present invention is applicable to the hip or spine, or to other sites of interest for bone fracture for which interventional threshold values of fragile-bone-strength are predetermined according to this invention, including the tibia, radius, ulna, humerus, wrist, and ankle. The method can also be applied to define and use interventional threshold values for any outcomes of a patient-specific finite element analysis of a patient's CT scan, for example, but not limited to, a strength, a stiffness, or a load-to-strength ratio, or for any other outcomes of any type of patient-specific bone structural or biomechanical analysis performed on any type of medical image, not necessarily a finite element analysis, and not necessarily a CT scan.

A system and method is presented for classifying a patient as having fragile-bone-strength. Preferably, finite element analysis is used to provide an estimate of the strength of a patient's bone using the patient's CT scan of their bone as input. Various different prior art methods exist to perform such a finite element analysis, as described in a number of references as noted above, including U.S. Pat. No. 5,172,695, and a phantomless calibration method can be used in part generate such models so that an external calibration phantom does not need to be used clinically, as described in U.S. patent application Ser. No. 14/311,242 (and in counterpart application number PCT/US14/43533) for "Quantitative Phantomless Calibration of Computed Tomography Scans" which claims benefit from U.S. Provisional Patent Application No. 61/838,159, all of which are hereby expressly incorporated by reference thereto in their entireties. Using a predetermined interventional threshold value for fragile-bone-strength, the patient is then classified as having or not having fragile-bone-strength. On this basis, the patient is optionally also classified, with or without information on the BMD of the patient's bone, as being either in a high-risk category for fracture or some lower risk category. The results are then written to a medical report and/or otherwise saved to computer medium. The medical report can optionally include information on the predetermined interventional threshold values for fragile-bone-strength.

Results from the virtual stress test can also be used to create dynamic virtual simulations of the bone's response to loading, for viewing by the patient, for example, using on-line viewing capabilities of some or all of the medical report on a display or monitor, or other renderer. Such dynamic simulations are performed for the patient's bone as it appears in their CT scan, and for various hypothetical future scenarios in which the patient's virtual bone is virtually altered to simulate various possible treatments, including no treatment at all. The latter can be used to estimate when the patient should next be tested if they test negative for fragile-bone-strength, so that they are tested next before they are likely to have fragile-bone-strength, in time to prescribe them a preventative treatment; timing in this way also avoids follow-up testing of patients while they are unlikely to have fragile-bone-strength.

One unique component of this invention is the use of a predetermined interventional threshold value of bone strength for the classification of fragile-bone-strength, and the related methods for defining such threshold values, and the values themselves. Without such interventional threshold values, a virtual stress test for bone strength, or any other structural analysis-based assessment of bone, cannot be used clinically in a consistent or widespread fashion to manage patients since physicians would not otherwise know how to interpret the results of the test, make a clinical decision as regards to managing the patient, or know whether or not to recommend the patient for treatment. Further, because of regulatory requirements, the development of any new strength or structural analysis test of bone for the medical management of patients can require lengthy and expensive fracture-outcome clinical studies just to develop an interventional threshold value. Then, additional fracture-outcome clinical studies need to be performed to prospectively validate any such threshold value, typically in multiple patient populations. Oftentimes this requirement becomes too expensive or takes too many years to fulfill, thus preventing new bone strength or structural analysis tests from being successfully introduced into clinical practice. This invention addresses these issues by exploiting what is already well accepted clinically about BMD regarding the definition of osteoporosis and classification of patients who are at high risk of fracture based on a classification of osteoporosis. It therefore enables powerful technologies such as finite element analysis of CT scans or other structural analysis tests of any type of medical image to be applied clinically to manage patients in a widespread and consistent fashion. For example, despite the long availability of finite element analysis of bone strength using CT scans, and various forms of bone structural analysis using DXA scans, those technologies have not yet been applied clinically to manage patients in a widespread and consistent fashion due in part to the lack of any prospectively validated interventional threshold values for such tests and the difficulty of interpreting the results clinically. This is true also for many types of bone structural analyses of many different types of medical images, including but not limited to all the incorporated references noted above.

Another unique component of this invention is that it enables results from different implementations of the finite element analysis technique, or alternate types of structural or biomechanical analysis of a patient's bone, to be used and still provide consistent classifications. This consistency—which results from the interventional threshold value of the new bone test corresponding statistically with the well characterized and widely validated and clinically accepted interventional threshold value for osteoporosis—is important in clinical practice since different implementations of what is essentially the same test need to provide at least as good a fracture risk assessment as does a classification of osteoporosis if the new test is to be widely and consistently used for medical decision making and management of patients. This enables different software versions of the same test to provide consistently good classifications, and different software vendors, who perform the virtual stress test in different ways, to also provide consistent classifications with each other.

Another unique component of this invention is that it enables results from the virtual stress test to be presented to a lay audience—typical patients—in such a way as to present an easily understood graphic visualization of the weakness of any patient's bones, for patients who are classified as having fragile-bone-strength. This feature takes what is an abstraction for the lay person—a numerical level of bone strength or some other quantitative structural measure of a bone or portion thereof—and makes it more immediately accessible to the patient. This feature is intended to help motivate patients to seek treatment, and stay on treatment, if they have fragile-bone-strength. It can also help patients understand the potential benefits of different treatment options, as applied to their own bones.

With knowledge of the predetermined interventional threshold, the medical report can also be used to estimate the timing for when a patient should be tested next in any follow-up test. This is achieved by comparing a present assessment of bone strength with the predetermined interventional threshold value on a chart that also displays typical population trends for how bone strength changes with age. Those trends can be matched to the demographic population of the patient at hand, for example, Caucasian women in the United States. In this way, use of a predetermined interventional threshold value for bone strength can be used to optimize the timing of such a follow-up test.

The method for determining the interventional threshold value for bone strength or any other structural measure that results from a structural analysis of a bone or portion of bone is based on defining the value of bone strength (or other structural measure) that corresponds to the BMD at the well-established interventional threshold value for BMD, namely, the BMD value (or T-score value) that clinically defines osteoporosis. This correspondence is found statistically for a population of patients that are typical of the target population of the new bone test, and will depend on the general statistical relation between bone strength and BMD for that population, which may be linear or non-linear. This method requires that there is a statistically significant relation between bone strength and BMD, namely a p-value of 0.05 or lower. Typically the resulting $R^2$ value in a linear or non-linear regression analysis should be 0.50 or above for good precision, but lower $R^2$ values can work so long as the relation is statistically significant at the $p \leq 0.05$ level of significance. This relation is then used to specify a unique value of bone strength from a value of BMD, in a statistically valid fashion. Thus, according to this method, the statistically significant relation between bone strength and BMD for a population is used to calculate a value of bone strength that corresponds to the well-established interventional osteoporosis threshold for BMD. That value of bone strength, or an approximately similar value, is then taken as the predetermined interventional threshold value for subsequently defining fragile-bone-strength in the clinical management of patients.

Of note, no fracture-outcome study is required to define this interventional threshold value—a simple cross-sectional study will suffice in which outcomes for the new test and the established BMD outcome (for defining osteoporosis) are both collected in a pairwise fashion for a population of multiple bones; no clinical outcomes are required. Such a study could be performed retrospectively on previously taken scans, or even on cadaver specimens. As noted above, adopting such an approach can substantially reduce the time and expense of defining the interventional threshold value compared to having to perform one or more fracture-outcome studies.

For any new test, if the probability of fracture for fragile-bone-strength in a prospective fracture-outcome study is found not to be as high as it is for osteoporosis, then the test may not be very useful clinically since it would be difficult to make a medical decision on patient care if the associated risk of fracture for fragile-bone-strength was less than the (well accepted) risk level associated with osteoporosis. Thus, in order to provide a clinically useful test, the following two conditions are ideally met when applying this method to the definition of an interventional threshold value for bone strength as defined herein: (a) there is a statistically significant relation between BMD and bone strength that enables specification of a statically valid value of bone strength from a value of BMD; and (b) the risk of fracture at the predetermined interventional threshold value for bone strength is at least as high as the risk of fracture at an established BMD-based interventional threshold value for osteoporosis. For this invention, the first condition is necessary, the second condition is merely desirable.

Another advantage of this method for defining the interventional threshold value for bone strength is that it is quite general. The outcome of the bone test does not have to be a value of bone strength per se, but instead can be any result of a structural analysis of a bone that is statistically significantly related to BMD, so that a statistical approach can be used to define a value of the bone structure outcome that corresponds to the well-established interventional threshold value of BMD for osteoporosis.

In one particular embodiment of this method, said value of bone strength is first calculated as described, and then is rounded up slightly to produce a rounded up value for the interventional threshold for defining fragile-bone-strength. This rounding up achieves two functions. First, it produces a number that is easier to remember and use clinically (e.g. 4,500 N versus 4,335 N). And second, it has the effect of classifying more patients with osteopenia as having fragile-bone-strength than if the lower, unrounded value were used for the interventional threshold value. This increases the sensitivity of the test and therefore further helps address the under-diagnosis problem; the small resulting decrease in specificity is typically of little clinical importance since therapeutic treatments for osteoporosis are all relatively safe. Alternatively, one could slightly round down, which would result in lower sensitivity but higher specificity—a more conservative classification. Thus, any value to within approximately ±20% of the statistically corresponding value can be defined as the interventional threshold value.

In another feature of this invention, the interventional threshold value for fragile-bone-strength is used with the interventional threshold value for osteoporosis to provide an overall fracture-risk classification for a patient. This can be done in at least two ways, depending on how conservative the overall clinical classification needs to be. In a more conservative approach, patients would be classified overall as being at high risk of fracture only if they were classified as having both osteoporosis AND fragile-bone-strength. In a less conservative approach, patients would be classified overall as being at high risk of fracture if they were classified as having either osteoporosis OR fragile-bone-strength. If the latter OR approach is used, the overall risk classification will capture a subset of patients with osteopenia—typically not considered at high risk of fracture if only BMD is considered—who nonetheless are at high risk of fracture because they have fragile-bone-strength. This is an important clinical feature of this invention. The more conservative AND approach may be more suitable in applications in which there is concern that too many low-risk patients (in actuality) are being identified as high risk on the basis of a problematic assessment of osteoporosis. Fracture risk assessment at the spine is a good example, since DXA for the spine is known to be limited due to the confounding effects of posterior elements, unusual vertebral geometry in some patients, and/or aortic calcification. The less conservative OR approach may be more suitable in other applications in which there is concern that too few high-risk patients (in actuality) are being identified as high risk on the basis of an assessment of osteoporosis that has low sensitivity. Fracture risk assessment at the hip is a good example, since DXA for the hip is known to have low sensitivity and thus identifies too few patients who are indeed at high risk of fracture. This type of overall classification of fracture risk can be included in the medical report and is made possible by knowledge of the predetermined interventional threshold values for both fragile-bone-strength and osteoporosis.

In another embodiment, a dynamic medical report is generated, namely, a medical report that depicts in some manner the results of an animation of the virtual stress test, or, the animation itself. Using data generated by the finite element analysis of the patient's bone, an animated image is generated showing deformation of said bone under the applied virtual loads corresponding to the interventional threshold value. For example, for a woman's femur, the virtual model of the proximal femur is loaded in a sideways fall configuration to the corresponding interventional threshold value for that bone and sex. For cases in which the estimated strength of said bone from the virtual stress test is less than or equal to the interventional threshold value, regions of said model are colored in proportion to the amount of bone tissue that fails in the model during the virtual simulation, the colors becoming more intense and more regions being colored as the level of external loading increases. Thus, the weaker the bone, generally, the more color is added. By contrast, for cases in which the estimated strength of said bone from the virtual stress test is greater than the interventional threshold value, very little if any of the bone model is colored during the virtual simulation. In both cases, the bone can also be visualized as deforming. The results can be written to a computer and viewed interactively or viewed as a video or by any other means of viewing dynamic animations. This feature is made possible by the use of a predetermined interventional threshold value for fragile-bone-strength.

In an additional embodiment, the effects of aging and treatment can also be simulated so as to visualize if various types of treatment can avoid fracture (and coloring of the bone). Such treatment effects can be applied in a generic fashion, based on available published scientific literature, or, using previously gathered data for other patients on various treatments and averaged in some manner, for example using a statistical atlas of changes. See for example, for application of a statistical atlas to describe local changes in bone density for a population, Carballido-Gamio (Proximal femoral density distribution and structure in relation to age and hip fracture risk in women. Carballido-Gamio J, Harnish R, Saeed I, Streeper T, Sigurdsson S, Amin S, Atkinson E J, Therneau T M, Siggeirsdottir K, Cheng X, Melton U 3rd, Keyak J, Gudnason V, Khosla S, Harris T B, Lang T F. J Bone Miner Res. 28:537-46, 2013), which is incorporated herein. Together, these types of dynamic simulations provide intuitive information that is easily understood by both patient and physician, and should better convey to the patient the current and future status of their bones. Additional types of simulations can similarly be viewed. A key feature of this invention is the integration of the interventional threshold values in these simulations, so that the patient is viewing their bone loaded by force levels defined in some way by the strength value at the interventional threshold value.

To facilitate clinical implementation of this process, a cloud-based delivery approach can be used so that the physician or radiologist does not have to perform the virtual stress test analysis themselves, and instead the analysis is performed remotely by a skilled technician. Such an approach also facilitates viewing of any dynamical medical report by a patient, who can use a web browser to access and view their own dynamic medical report. In one embodiment, a CT scan is taken of the patient and sent electronically to a remote location, which could be in another part of the hospital or imaging facility or far away. Said scan is analyzed by virtual stress testing at said remote location and the medical report is then sent back electronically to the hospital or ordering physician or uploaded on a secure web site for secure access by a physician or patient, said report containing information on the comparing of the patient's bone strength with the interventional threshold value for fragile-bone-strength, thus facilitating clinical interpretation. Using this cloud-based delivery approach, a single remote facility can provide the same type of standardized virtual stress test with its dynamic medical report—using the same software version, run in the same way, and operated by the same technicians—to many different hospitals. In that way, the results of the test are easily standardized and compared across the many different hospitals, despite the technical complexity of the test, and easily accessed and viewed by a physician or patient. Patients can also view their dynamic medical report via a centralized web site.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying Figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Figure 1:
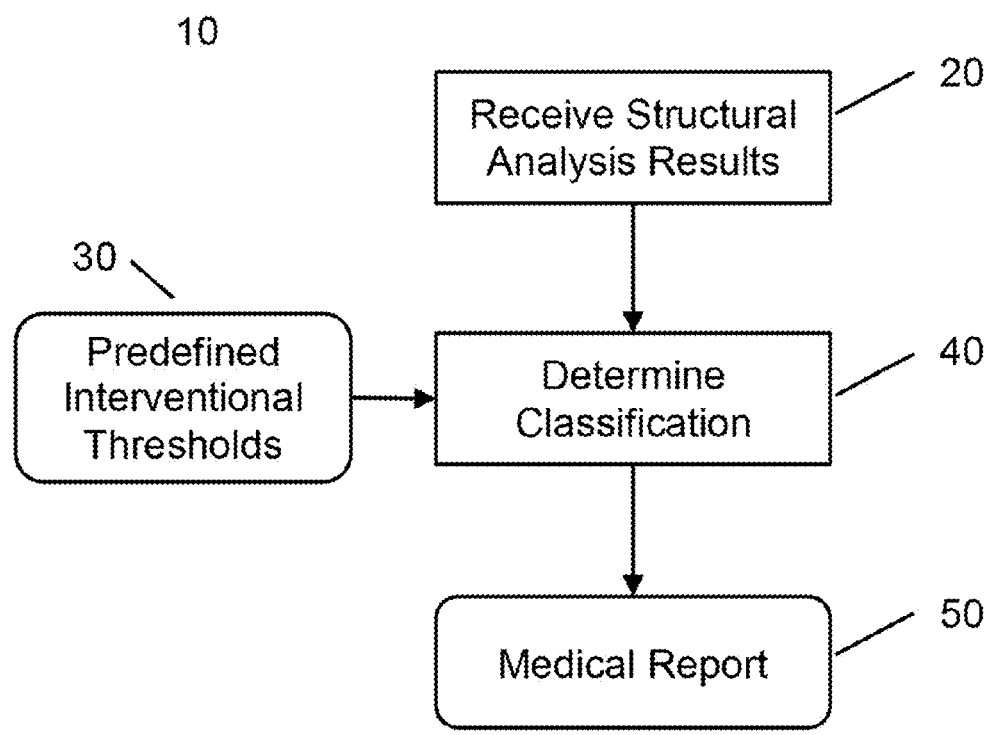
FIG. 1 illustrates a system in which the results of a structural analysis of a patient's bone, or portion thereof, are used in conjunction with a predetermined interventional threshold value to classify the patient for fragile-bone-strength, the results written to a medical report.

Embodiments of the present invention provide a system and method for the use of the results from a structural analysis of a patient's bone from a medical image of a patient's bone or portion thereof, as depicted in FIG. 1, to be used clinically to manage patients. The invention utilizes a comparison of a measurement from this analysis versus an interventional threshold value for fragile-bone-strength to classify a risk of fracture, allowing for more people at high risk of fracture to be identified than would be possible if only a BMD measurement were used. Some embodiments also describe medical reports that can help patients better understand their risk of fracture. The following description is presented to enable one of ordinary skill in the art to make and use the invention and is provided in the context of a patent application and its requirements.

Various modifications to the preferred embodiments and the generic principles and features described herein will be readily apparent to those skilled in the art. Thus, the present invention is not intended to be limited to the embodiments shown but is to be accorded the widest scope consistent with the principles and features described herein.

DEFINITIONS

The following definitions apply to some of the aspects described with respect to some embodiments of the invention. These definitions may likewise be expanded upon herein.

As used herein, the term "or" is generally intended to mean "and/or" unless otherwise indicated.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the terms "approximate" and "approximately" in the context of a strength value or a structural measure value for a bone and results derived from an assessment as described herein, for example in the discussion of FIG. 7 and FIG. 8, includes scope of statistical variation of that strength value or structural measure value that the subsequently described event or circumstance may or may not occur, and for some implementations of the present invention corresponds to ±20% about the statistically prescribed value or as noted otherwise.

As used herein, the term "interventional threshold value" (or equivalent) in this invention refers to a specific numerical level of a measured structural parameter from a bone analysis that can be used clinically by a qualified physician to identify patients who are suitable candidates for medical intervention, typically some type of therapeutic drug treatment, or to otherwise make a medical decision in the management of the patient. The use of this specific term herein should not be construed to limit the invention only to this specific term, but instead should be interpreted more broadly to encompass any substantially similar other term having substantially similar clinical meaning. Such other terms include but are not limited to: therapeutic cut points, interventional cut points, diagnostic thresholds, target levels, or any combinations or permutations of such.

As used herein, the term "bone strength" should not be construed to limit the invention only to the literal meaning of this term. Instead our use of said term should be interpreted more broadly to encompass any type of numerical outcome from a finite element analysis or any other type of structural or biomechanical analysis of a patient's bone or portion thereof, said analysis performed using a clinical CT exam or any other type of clinical scan or medical image of said patient's bone or portion thereof. Such analysis outcomes include but are not limited to measures of: a strength, a stiffness, an energy, a load-to-strength ratio, a safety factor (or factor of safety), an amount or proportion of damaged tissue, a force, a bending moment, a torsion, a fatigue strength, an endurance limit, a stress, a strain, a strain energy density, a deformation, a length, a diameter, a thickness, an area, an areal moment of inertia, a mass moment of inertia, a density-weighted moment of inertia, a modulus-weighted moment of inertia, a section modulus, a flexural stiffness, a bending stiffness, an axial stiffness, any quantitative measure of trabecular microarchitecture, a trabecular thickness or spacing, a trabecular bone score, a fracture index score, a neck axis length, a buckling ratio, a cortical thickness, a ratio of cortical to trabecular bone mass, a plate-to-rod ratio, or any combination thereof. Any such measures can be normalized by a patient parameter, including but not limited to a weight, a height, an age, or a body-mass-index. Thus, depending on the context, it should be obvious to one of ordinary skill in the art that the use of this specific term herein should not be construed to its most narrow and literal meaning but instead should be interpreted more broadly as should be obvious from the context.

As used herein, the term "fragile-bone-strength" is defined as the level of bone strength—or a value of some other quantitative measure of bone structure—that corresponds statistically to a level of bone mineral density (BMD) that clinically defines osteoporosis. Such measures of BMD can be expressed as measures of areal density (in g/cm2), volumetric density (g/cm3), or T-scores. Patients are said to have "fragile-bone-strength" when their bone strength—or a value of some other measure of bone structure—is less than or equal to the threshold value for fragile-bone-strength, which serves clinically as an interventional threshold value. The use of this term should be construed to apply both to a threshold value of bone strength, per se, and also to any quantitative measure of "bone strength" as defined in the previous paragraph. For example, if the structural analysis test provides an outcome measure of cortical thickness, then the term "fragile-bone-strength" as used herein would be construed to refer to the interventional threshold value for cortical thickness. As used herein, the term can be used to refer to a value of an interventional threshold and to a condition. For example, as the term is used herein, a patient is said to have fragile-bone-strength if their bone strength is less than or equal to the threshold value for fragile-bone-strength.

As used herein, the term "dynamic medical report" is used to denote a medical report that contains some form of visual information resulting from a virtual stress test of a patient's bone. For example, this report may comprise of a paper report, or equivalent electronic version, that contains one or more still images taken from the virtual stress test, for example, images of a virtual model of a patient's bone at one or more stages of the virtual stress testing. Or, this report may comprise of an animation of the virtual stress test of a virtual model of the patient's bone.

As used herein, unless qualified specifically, the terms "medical image" or "scan" or "exam" are used to mean substantially the same thing, namely, some type of digital image of a body part, typically taken of a live patient for some medical purpose. For most embodiments described, this image comprises a CT scan (also referred to sometimes as a CT exam), but in some instances it can refer to a DXA scan (also referred to sometimes as a DXA exam), an ultrasound scan, an X-ray, or an MRI scan. Unless expressly noted or specifically qualified, these terms should be afforded the more general meaning as referring to any of these image types, and should not be construed to apply just to a CT scan, as should be obvious from the context to one of ordinary skill in the art.

Examples of applications of this invention are described for clinical management of osteoporosis, focusing on the hip (femur) and lumbar spine. However, the present invention may also be applied to any type of medical condition for which bone strength potentially plays an important role in a clinical outcome and for which a predetermined interventional threshold value is used for clinical management of patients. For example, the invention can also be applied to different types of bones other than the femur and vertebra, including but not limited to: the ankle, tibia, pelvis, thoracic and cervical spine, wrist, and humerus. As noted above, it can also be applied to the results from a bone structural analysis of clinical scans other than clinical CT scans, for example, DXA scans, MRI scans, X-rays, or ultrasound scans. In the following description, numerous specific details are set forth in order to provide a thorough understanding of the present invention. It will be apparent, however, to one skilled in the art, that the present invention may be practiced without some or all of these specified details and may be applied to any medical application in which interventional threshold values for bone strength are required for clinical application and management of patients. In some instances, well-known steps of finite element modeling, engineering structural analysis, bone biomechanics, and medical image processing have not been described in detail in order to not unnecessarily obscure the present invention. The following detailed descriptions are presented to enable one of ordinary skill in the art to make and use the invention. Various modifications to the embodiments will be readily apparent to those skilled in the art, only some of which are depicted in the Figures. Thus, the present invention is not intended to be limited to the embodiments shown but is to be accorded the widest scope consistent with the principles and features described herein.

Figure 2:
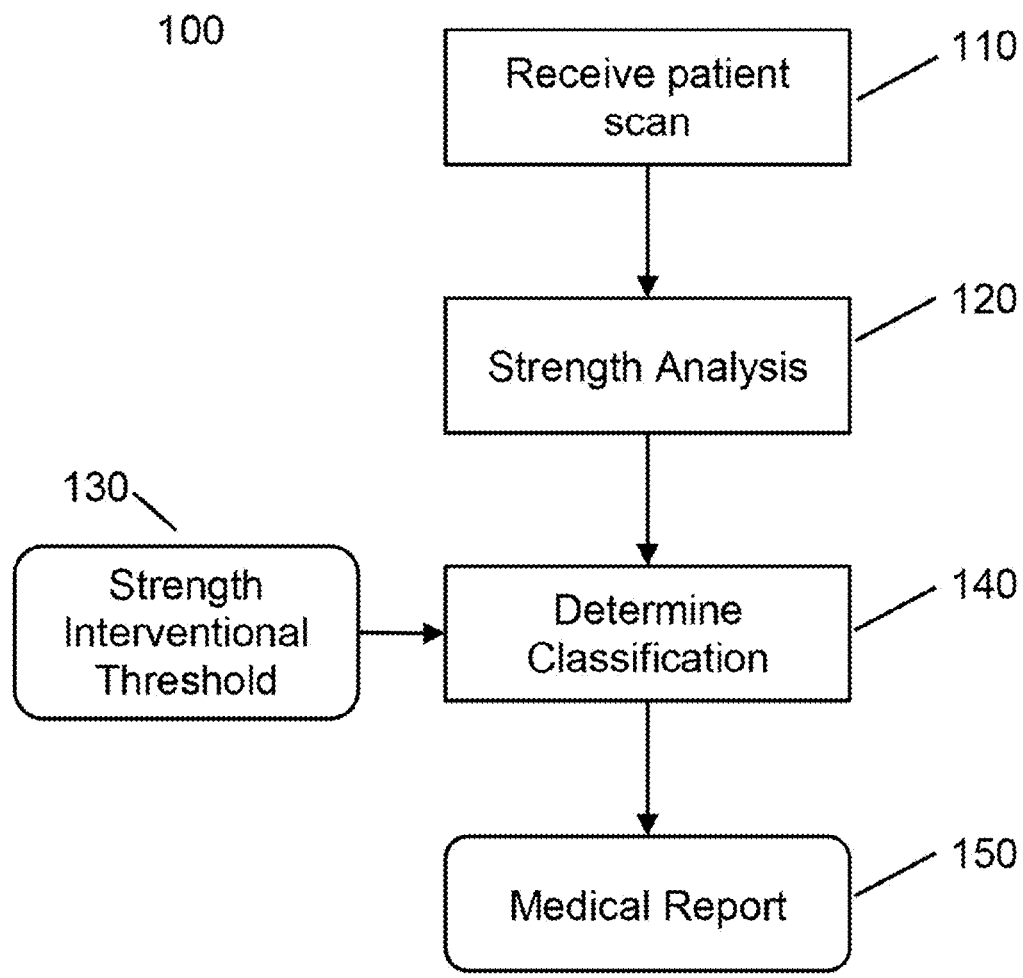
FIG. 2 illustrates a system in which a strength analysis is performed using a medical image of a patient's bone or portion thereof in order to classify for fragile-bone-strength by comparison to a predetermined interventional threshold value for fragile-bone-strength, the results written to a medical report.

One specific embodiment, as depicted in FIG. 2, is a system 100 in which a medical image or scan 110 of a patient's bone or portion thereof is received and used to provide results for the classification. This medical image, preferably a CT scan, but in some instances a DXA scan, ultrasound scan, X-ray, or MRI scan, covers at least one bone or bone portion of interest, such as a femur, a proximal femur, or a vertebral body, for which strength will be measured. Using the medical image as input, a strength analysis 120 is performed in order to determine a value of strength of the patient's bone portion. A comparison of that strength measurement is then made against a predetermined interventional threshold value for strength 130 in order to determine a classification for fragile-bone-strength. A single interventional threshold value would demarcate two classification categories (e.g. fragile-bone-strength vs. not-fragile-bone-strength); two interventional threshold values would demarcate three classification categories (e.g. fragile-bone-strength vs. low-bone-strength vs. normal-bone-strength); and so forth. A medical report containing the test results is then created, and can optionally further classify a patient as being at high risk of fracture based on the classification of fragile-bone-strength.

In a variation of this embodiment, multiple bones can be analyzed per medical scan, for example two hips. Each hip can be classified for fragile-bone-strength, and the patient's overall risk of fracture can be based on these two classifications. For example, if either hip is classified as being in the fragile-bone-strength category, the patient is classified as being at high risk of fracture. Similarly, for multiple vertebral levels, multiples bones can be analyzed. In this case, since vertebral strength varies with vertebral level, each level may have its own pre-determined interventional threshold value for defining fragile-bone-strength. Again, if any vertebral level is classified as being in the fragile-bone-strength category, the patient is classified as being at high risk of fracture.

Figure 3:
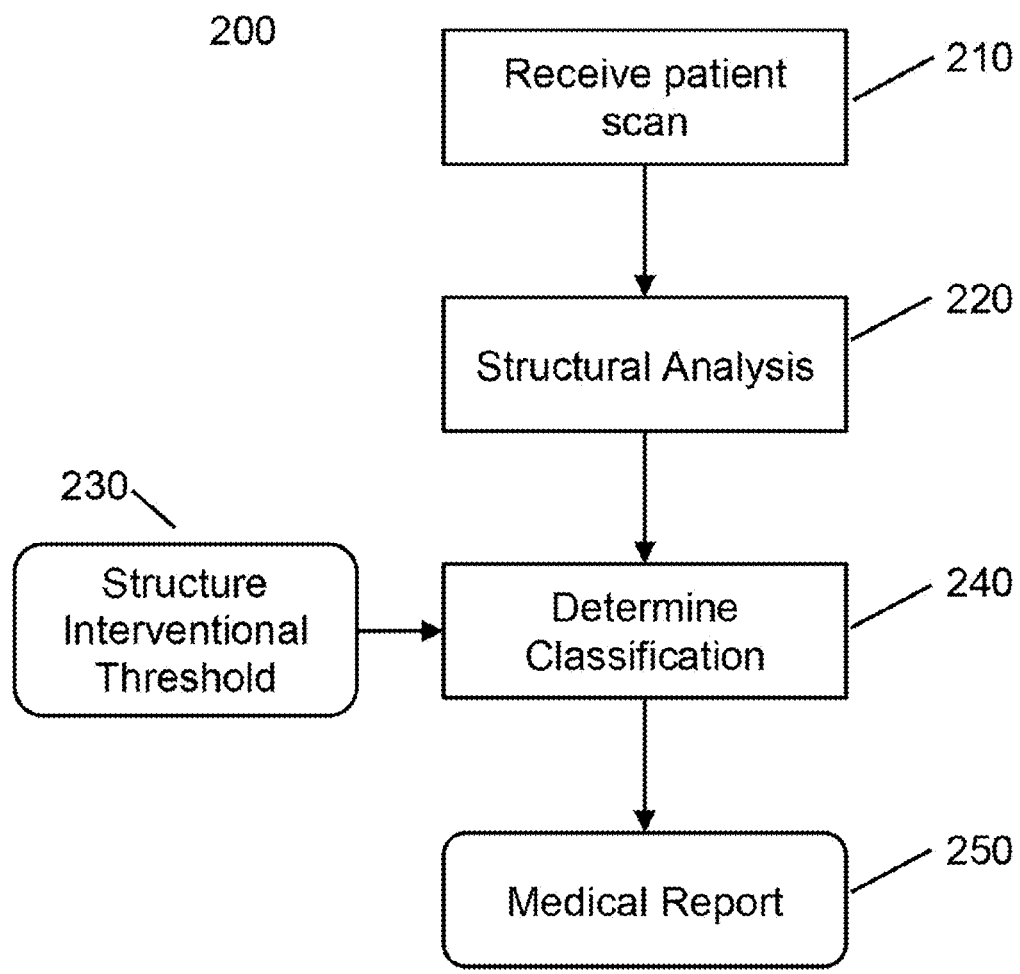
FIG. 3 illustrates a similar system as in FIG. 2 wherein instead a structural analysis is performed and a result of said structural analysis is compared with a predetermined interventional threshold value for said type of result.

Another embodiment, as depicted in FIG. 3, is a system 200 similar to system 100 except that a structural analysis 220 is performed instead of specifically a strength analysis 120. The structural analysis quantifies any structural characteristic of the bone, providing outcomes such as those noted above for the defined term "bone strength". For example, an MRI scan could be analyzed to provide a measure of a bone area; a CT scan could be analyzed to provide a measure of a bone area, and, a strength-type measure could be calculated as the product of said area and a density squared of the bone contained within the area; a DXA scan could be analyzed to measure a hip femoral neck axis length, a buckling ratio, or a trabecular bone score (often abbreviated as TBS); or an X-ray could be analyzed to measure a variety of bone density and microstructural parameters and from that calculate a fracture index score. Various prior art references could be used for such purposes, including but not limited to: Bousson (2008, 2012), Wehrli (2001), Kazakia (2008), Pothuaud (2008), and US patent application U.S. Ser. No. 11/855,939 and U.S. Pat. No. 8,073,521, all of which are incorporated herein by reference. A classification 240 of fragile-bone-strength is then determined by comparing these structural measures to their corresponding, predetermined interventional threshold values 230. The medical report 250 is similar to medical report 150 except that structural measures and their related classifications are reported instead of values associated with a strength measure.

Figure 4:
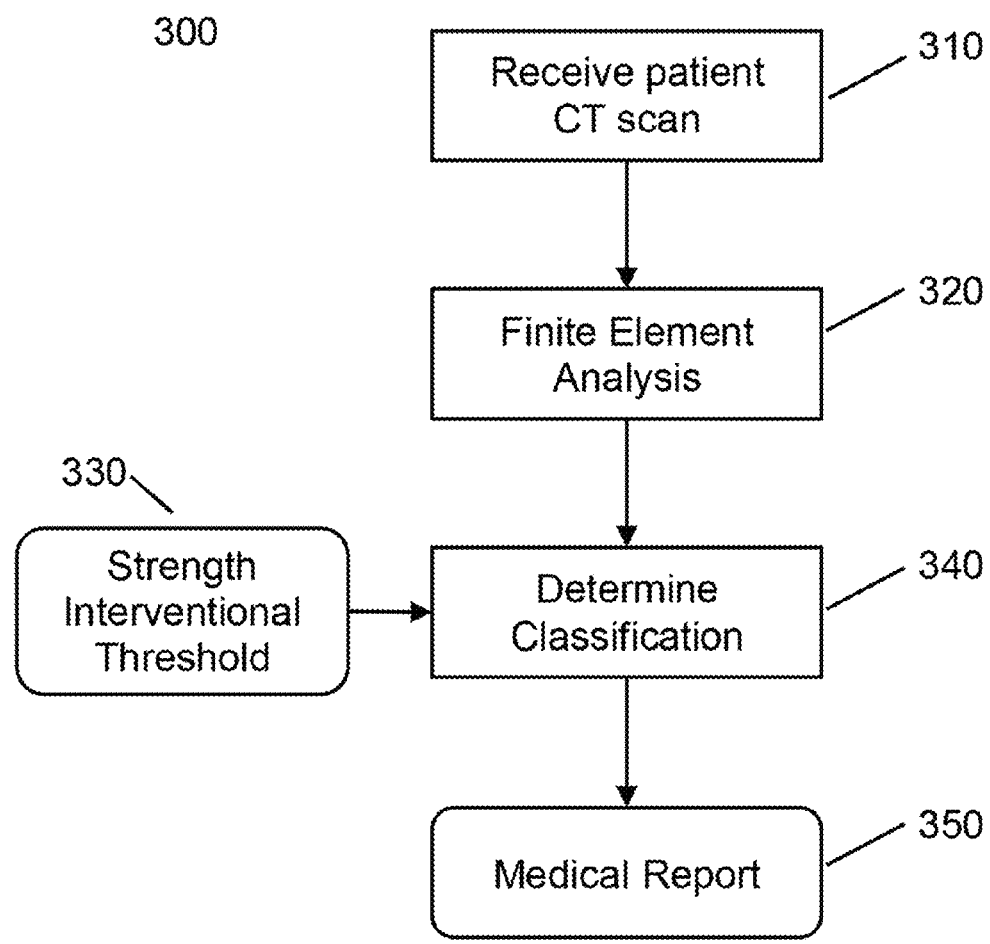
FIG. 4 illustrates a system similar to the system in FIG. 2 wherein the strength analysis is a finite element analysis and said medical image is a CT scan.

Another embodiment, as depicted in FIG. 4, is a system 300 similar to system 100 wherein the patient scan 110 is specifically a clinical CT scan 310, and the strength analysis 120 is specifically a patient-specific finite element analysis 320. As described in the references incorporated herein, imaging processing steps are performed to create a finite element model from a clinical CT scan covering the bone or bone portion of interest. The finite element model is virtually subjected to certain loading conditions in order to obtain a measurement of strength or another structural parameter for that loading condition. The femur, for example, may be loaded in a stance or a sideways fall configuration to obtain a stance or fall strength, respectively. Other steps in the system proceed in a manner similar to corresponding steps in system 100.

For system 300, one particular embodiment is to construct finite element models of the proximal femur and L1 vertebral body implementing a similar finite element modeling approach to the one described by Keaveny (Keaveny T M, McClung M R, Genant H K, Zanchetta J R, Kendler D, Brown J P, Goemaere S, Recknor C, Brandi M L, Eastell R, Kopperdahl D L, Engelke K, Fuerst T, Radcliffe H S, Libanati C. Femoral and vertebral strength improvements in postmenopausal women with osteoporosis treated with denosumab. J Bone Miner Res. 29:158-65, 2014), hereby incorporated by reference. For such an implementation of the finite element analysis, or any substantially similar implementation, or for any non-invasive bone strength test that provides values of a compressive strength for a vertebral body or a sideways fall strength for a proximal femur, wherein said strength values are substantially the same as those values obtained from direct biomechanical testing (for example, in cadaver experiments that have similar boundary conditions to those used in the finite element-based virtual stress tests in the above-referenced Keaveny 2014 study), the following predetermined interventional threshold values can be used to define fragile-bone-strength (in units of Newtons, N): hip strength—3,000 N for women and 3,500 N for men; L1 vertebral strength—4,500 N for women and 6,500 N for men. These vertebral interventional strength thresholds are also applicable to the T12-L3 vertebral levels since these vertebrae are similarly sized to L1; lower values are recommended at more proximal vertebral levels (towards the head), and higher values at more distal vertebral levels (towards the pelvis).

Figure 7:
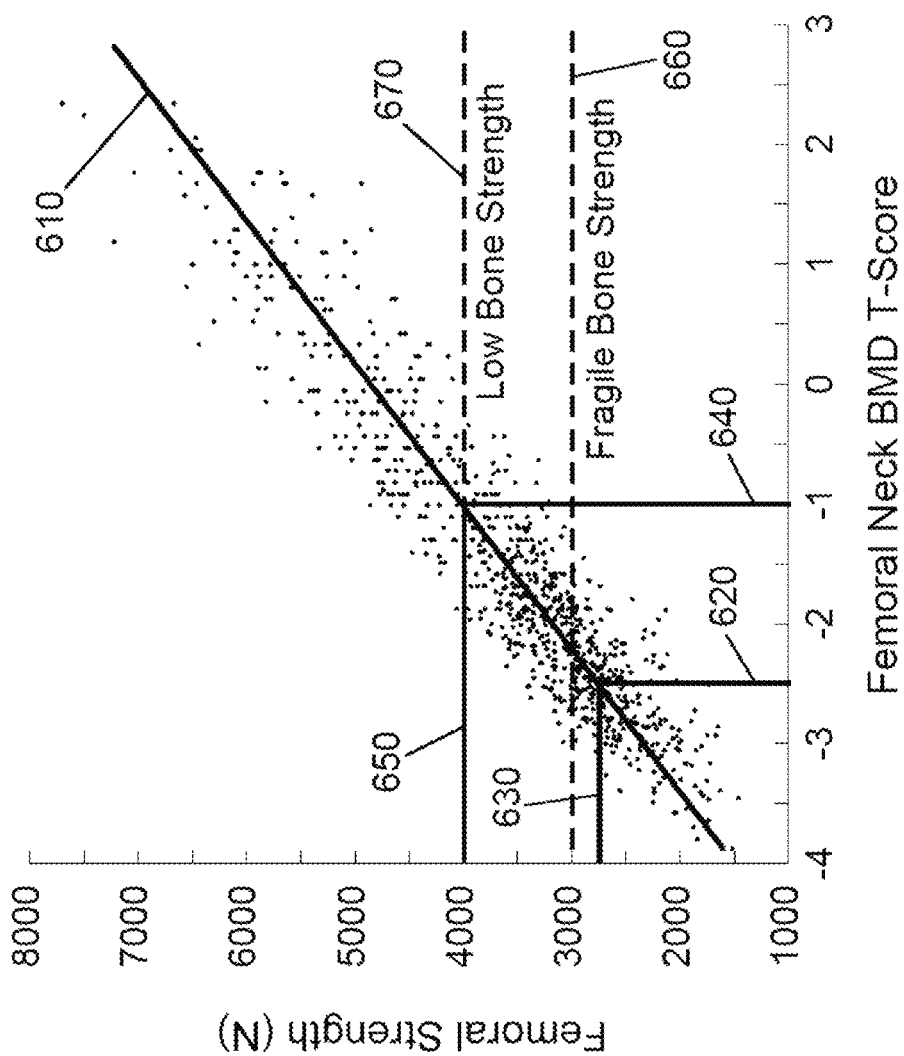
FIG. 7 illustrates an example of how data for the hip are used for the process shown in FIG. 6, in which a linear statistical correspondence exists between a strength and a BMD T-score.

Based on typical variations in the relationship between strength and BMD, as shown in FIG. 7, predetermined interventional threshold values for fragile-bone-strength approximately similar to the values noted in the previous paragraph can also be defined for successful clinical implementation. The range of scatter in the plots shown in FIG. 7 demonstrates a range of such approximately similar values. For femoral strength, it is seen that the interventional threshold values chosen to be used clinically for fragile-bone-strength could reasonably vary from about 2,300-3,500 N, about ±600 N from the statistically prescribed average value. For example, such a range might arise from the need to be more conservative or liberal in classifying patients for fragile bone strength; or, to enable different tests to provide substantially the same clinical classifications despite using different types of measures of bone strength. This range corresponds to approximately ±20% of the statistically prescribed average value. This 20%-approach enables the technique to be applied to any approximately accurate measure of strength, whether fall or stance for the hip, or compression or bending for the spine. For other bone strength measures, for example, a load-to-strength ratio or a cortical thickness or a buckling ratio or a TBS score, a reasonable range of approximate values of a predetermined interventional threshold value for fragile-bone-strength can be obtained by calculating the bone strength value associated with a BMD value falling approximately one third the way between the BMD threshold values for osteoporosis and osteopenia, and then using the statistical relation between BMD and bone strength to calculate the associated bone strength values for that range, above and below the statically prescribed value. For example, a femoral neck BMD T-score of approximately −2.0 falls one third the way between values of −2.5 (for osteoporosis) and −1.0 (for osteopenia), indicating and range of ±0.5 T-score units. The bone strength values in FIG. 7 for that range correspond to approximately ±500 N, similar but slightly more conservative to the range suggested in the previous paragraph. Likewise, for vertebral trabecular BMD, the BMD threshold values for osteoporosis and osteopenia are 80 and 120 $mg/cm^3$, respectively, suggesting a range of approximately ±15 $mg/cm^3$. It should be obvious to one of ordinary skill in the art that this method of setting a range about reasonable values of the statistically prescribed interventional threshold value is similarly applied to other outcomes measures from a finite element analysis, for example but not limited to: a strength for an alternative set of boundary conditions, a strength divided by a body-weight, a stiffness, a load-to-strength ratio, an energy, or a deformation.

Figure 5:
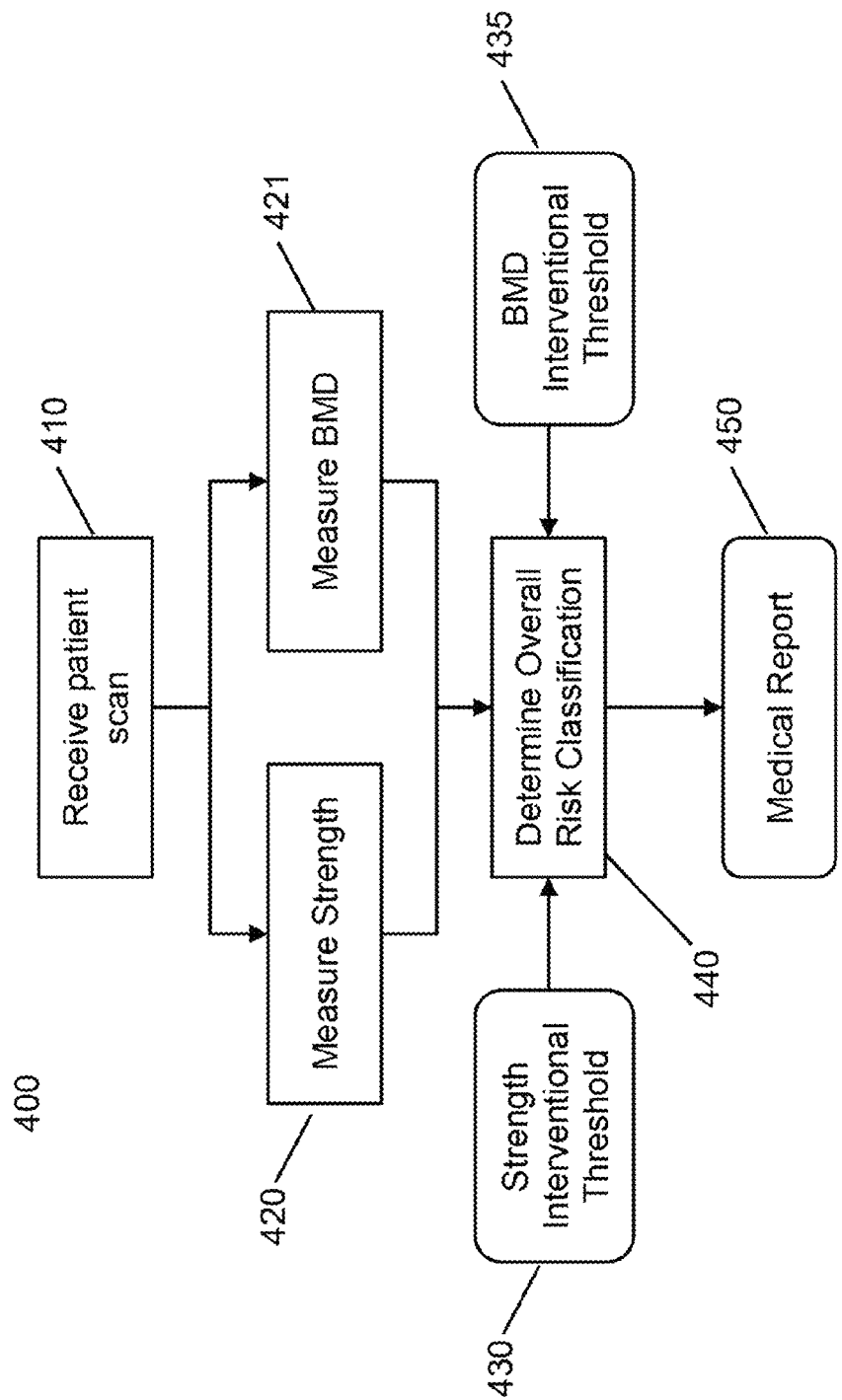
FIG. 5 illustrates a system for classifying an overall fracture risk based on classifications of both fragile-bone-strength (from a strength analysis) and osteoporosis (from a BMD analysis), using their respective interventional threshold values.

Another embodiment, as depicted in FIG. 5, is a system 400 similar to system 100, except that a BMD 421 is also measured and used with an established BMD interventional threshold value 435 in the determination of an overall risk classification 440. Using the patient scan 410 as input, a strength 420 is measured and a BMD 421 is measured. A CT scan or a DXA scan of the patient's bone could be used to measure BMD, as described for example by Khoo (Comparison of QCT-derived and DXA-derived areal bone mineral density and T scores. Khoo B C, Brown K, Cann C, Zhu K, Henzell S, Low V, Gustafsson S, Price R I, Prince R L. Osteoporos Int. 20:1539-45, 2009), which is incorporated herein by reference. The same scan or a different scan could be used for the BMD and bone strength measurements. If CT is used, the BMD measure could be a volumetric measure of BMD measured from the 3D data in the CT scan (for example, trabecular BMD in the spine, having an established interventional threshold value of 80 mg/cm3) or it could be a DXA-equivalent areal BMD measured from a DXA-like projection of the CT scan (for example, femoral neck areal BMD, having an established interventional threshold value T-score of −2.5). A finite element analysis could be used for the strength measurement, based on either a CT or DXA exam, the latter for example as described by Yang (Yang L, Peel N, Clowes J A, McCloskey E V, Eastell R. Use of DXA-based structural engineering models of the proximal femur to discriminate hip fracture. J Bone Miner Res. 24:33-42, 2009), which is incorporated herein by reference.

When determining the overall fracture risk classification 440, the strength measure is compared to the predetermined interventional threshold value for fragile-bone-strength 430 and the BMD measure is compared to the established interventional threshold value for osteoporosis based on the BMD measure (or a BMD T-score) 435. In this way, classifications are made separately for fragile-bone-strength and osteoporosis. These two classifications are then used together to make an overall fracture risk classification. For example, an individual may be considered at high risk of fracture if they have either fragile-bone-strength OR osteoporosis; or, more conservatively, if they have both fragilebone-strength AND osteoporosis. A medical report 450 is then written to computer medium, said report including these results and classifications, and may optionally display the interventional threshold values in some manner, either as numerical values or graphically.

Figure 6:
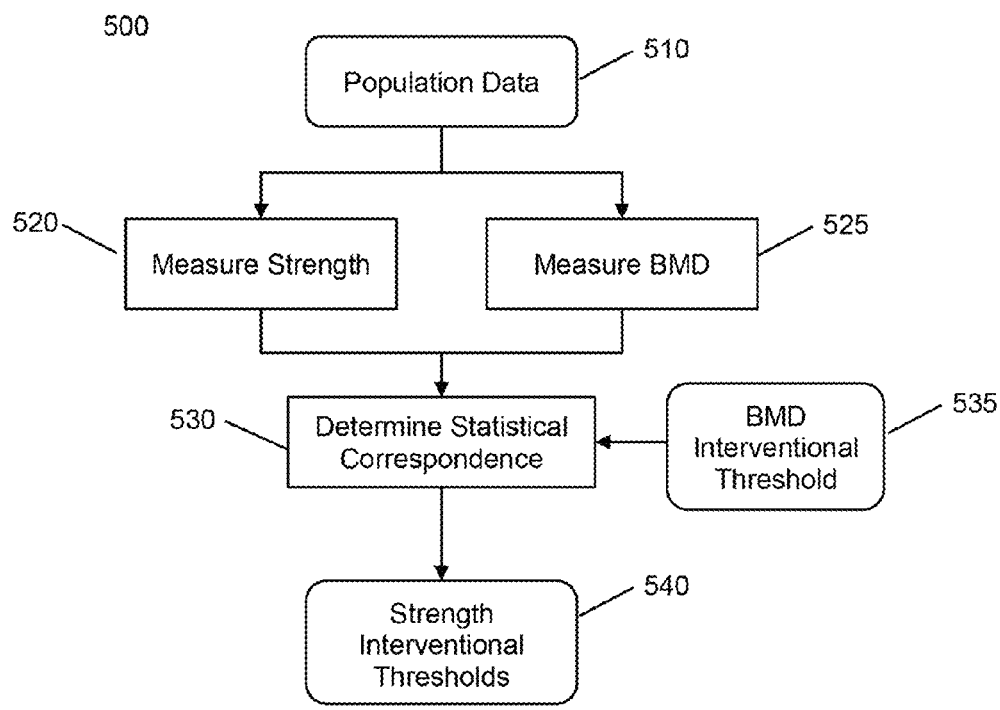
FIG. 6 illustrates a method for determining a value of an interventional threshold for fragile-bone-strength for a population of bones based on a statistical correspondence to the interventional threshold value for BMD that defines osteoporosis.

Another aspect of the invention is a system and method for constructing interventional threshold values. One embodiment, as depicted in FIG. 6, is a method 500 for defining the interventional threshold values for a measure of bone strength. The method uses population data 510 as input. These data include medical scans for each subject in the population, covering at least one bone of interest or portion thereof, and may also include demographic information for each subject, such as age, sex and race. This population data set could comprise scans and data from live people, for patients receiving medical care, for research subjects in a research study, or from cadaver bones. From each subject, a strength 520 is measured, and a BMD 525 is measured. As with process 400, the same scan or even different types of scans can be used for the BMD analysis and the strength analysis—all that matters is that, for the same subject, both a measure of BMD and a measure of strength are obtained; the specific medical image source of that information is not critical. Thus, for example, a DXA scan could be used for the BMD measurement, and a CT scan could be used for the strength measurement. Although it is preferable for the same bone to be analyzed for both BMD and strength, it is also possible that different bones could be analyzed. Thus, for example, a BMD measure could be obtained for the hip, and a strength measure could be obtained for a vertebra in the spine; or a BMD measure could be obtained for a lumbar vertebra, and a strength measure could be obtained for a thoracic vertebra. A statistical correspondence between these paired strength and BMD measures is then developed in 530. This correspondence may be, for example, a least-squares curve fit to the data, either linear, as shown for real data in FIG. 7, or non-linear, as shown for real data in FIG. 8. This statistical correspondence is then used together with an established interventional threshold value for the measure of BMD 535 to specify an interventional threshold value for strength 540. For example, if the correspondence is a linear regression between strength and BMD, then the interventional threshold value for fragile-bone-strength is defined as the strength value from the linear equation that results when the BMD at the osteoporotic threshold is used as the input independent variable. This interventional threshold value for fragile-bone-strength can be used as the predetermined interventional threshold value for bone strength in processes 130, 230, 330, and 430, as described above.

Figure 8:
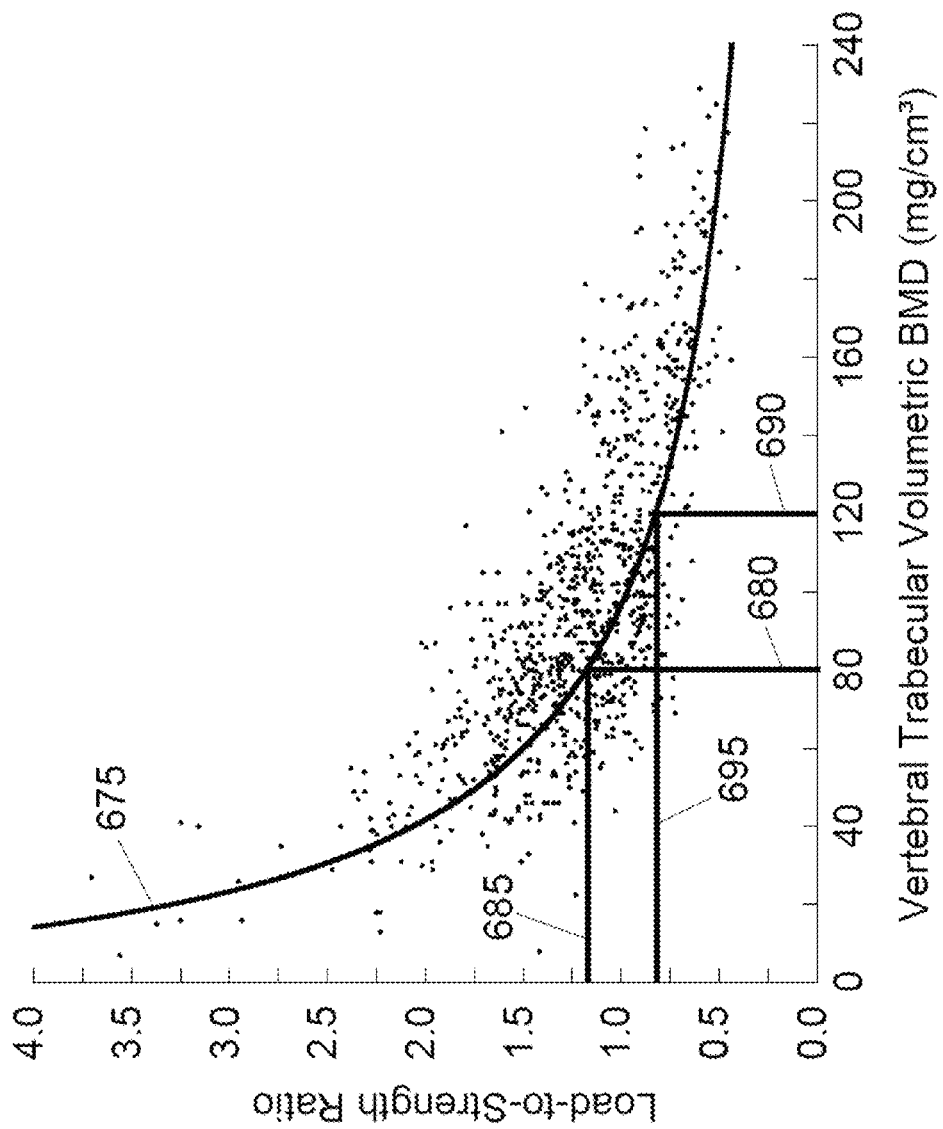
FIG. 8 illustrates an example of how data for the spine are used for the process shown in FIG. 6, in which a nonlinear statistical correspondence exists between a load-to-strength ratio and BMD.

The statistical correspondence used to derive strength-based interventional threshold values for fragile bone from the BMD-based interventional threshold values for osteoporosis can take various forms, as shown in FIGS. 7 and 8. One such correspondence is a linear regression 610 between femoral strength for a simulated sideways fall, obtained by a virtual stress test using finite element analysis of CT scans, and the femoral neck BMD T-score, obtained from quantitative analysis of the same CT scans; data are shown for over 800 women spanning a wide age range. Based on the least-squares linear regression 610 for these data, a strength value 630 of 2,770 N corresponds statistically to a BMD T-score 620 of −2.5, the established interventional threshold value for osteoporosis when the BMD measure comprises a femoral neck BMD T-score. This strength value can be defined as an (average) interventional strength threshold for fragile-bone-strength. Optionally instead, this strength value can be rounded up slightly 660 to a value of 3,000 N. Doing so has two positive effects. First, it produces a number that is easier to remember and use clinically (e.g. 3,000 N vs. 2,770 N). And second, use of the slightly higher value has the effect of classifying slightly more patients as having fragile-bone-strength. Some of those newly identified subjects from rounding up are in the osteoporosis category (T≤−2.5) and some are in the osteopenia category (−2.5<T<−1.0). Thus, rounding up can help identify additional patients with fragile-bone-strength who have osteopenia. This strategy would be appropriate at the hip, for which the BMD-defined osteoporosis classification provides only low sensitivity in correctly predicting who will eventually fracture their hip. In addition, the linear regression 610 can be used to define a strength threshold 650 corresponding to the BMD threshold 640 for osteopenia (T=−1.0 is the BMD threshold for osteopenia). The rounded-up value 670 is unchanged for this analysis. While femoral neck BMD T-score is preferable for defining osteoporosis in a hip fracture application, other BMD measures may be more appropriate depending on the anatomic site and the type of fracture. For example, for a spine fracture application, volumetric trabecular BMD for the spine is known to be a better predictor than the DXA BMD T-score. One could also round down the threshold values, which would decrease sensitivity but increase specificity. Such an approach might be preferable at the spine, for which BMD tends to produce many false positives and thus an improved specificity would be clinically beneficial in reducing the number of patients who are treated but who may not need or benefit from treatment.

The statistical correspondence process does not require a linear fit between BMD and strength, and the outcome of the structural analysis does not have to be a measure of strength per se (measured in Newtons). FIG. 8 shows a nonlinear curve fit 675 between a load-to-strength ratio for the spine and vertebral trabecular volumetric BMD, for over 800 women spanning a wide age range. The load-to-strength ratio is the ratio of the estimated spinal force during a lifting activity to the strength of the bone, obtained from finite element analysis of the CT scan; higher values are associated with a higher risk of fracture. This estimate of the spine force can be calculated using information on the patient's weight and height, and a simple biomechanics model comprising a stick-figure model of a human lifting an object with arms outstretched and in static equilibrium. The BMD in this plot is also measured from the same CT scan from the same bone as used in the finite element analysis. On this plot, a load-to-strength ratio 685 of 1.2 statistically corresponds to a BMD 680 of 80 mg/cm3, the established interventional threshold value for spinal osteoporosis, and is taken as the interventional threshold value for fragile-bone-strength. In addition, the nonlinear regression 675 can be used to define a threshold value 695 of the load-to-strength of 0.8 corresponding to the BMD threshold 690 for spinal osteopenia (120 mg/cm3 is the BMD threshold for osteopenia).

With knowledge of the threshold values for fragile-bone-strength, one can apply this invention to identify patients who have osteopenia by BMD criteria, but who are nonetheless at high risk of fracture due to the presence of fragile-bone-strength. In one embodiment, a patient is tested first with DXA to provide a measure BMD, which is compared against the osteoporosis thresholds. If the patient tests negative for osteoporosis, but they have osteopenia, they are sent for a bone strength test, which is obtained by finite element analysis of a CT scan and a value of bone strength is thus obtained. The CT scan may have already been taken for the patient as part of their previous medical care. In that case, the scan is re-analyzed and a value of bone strength is obtained. Some form of phantomless calibration scheme can be used to calibrate the previously taken CT scan if an external calibration was not simultaneously scanned with the patient. Or, a new CT scan is ordered for the patient, and the resulting new scan is analyzed and a value of bone strength is obtained. With either option, the bone strength value is compared against the threshold value for fragile-bone-strength, thus identifying osteopenic patients who have fragile-bone-strength. These analyses can be performed at the hip, spine, or both sites.

Figure 9:
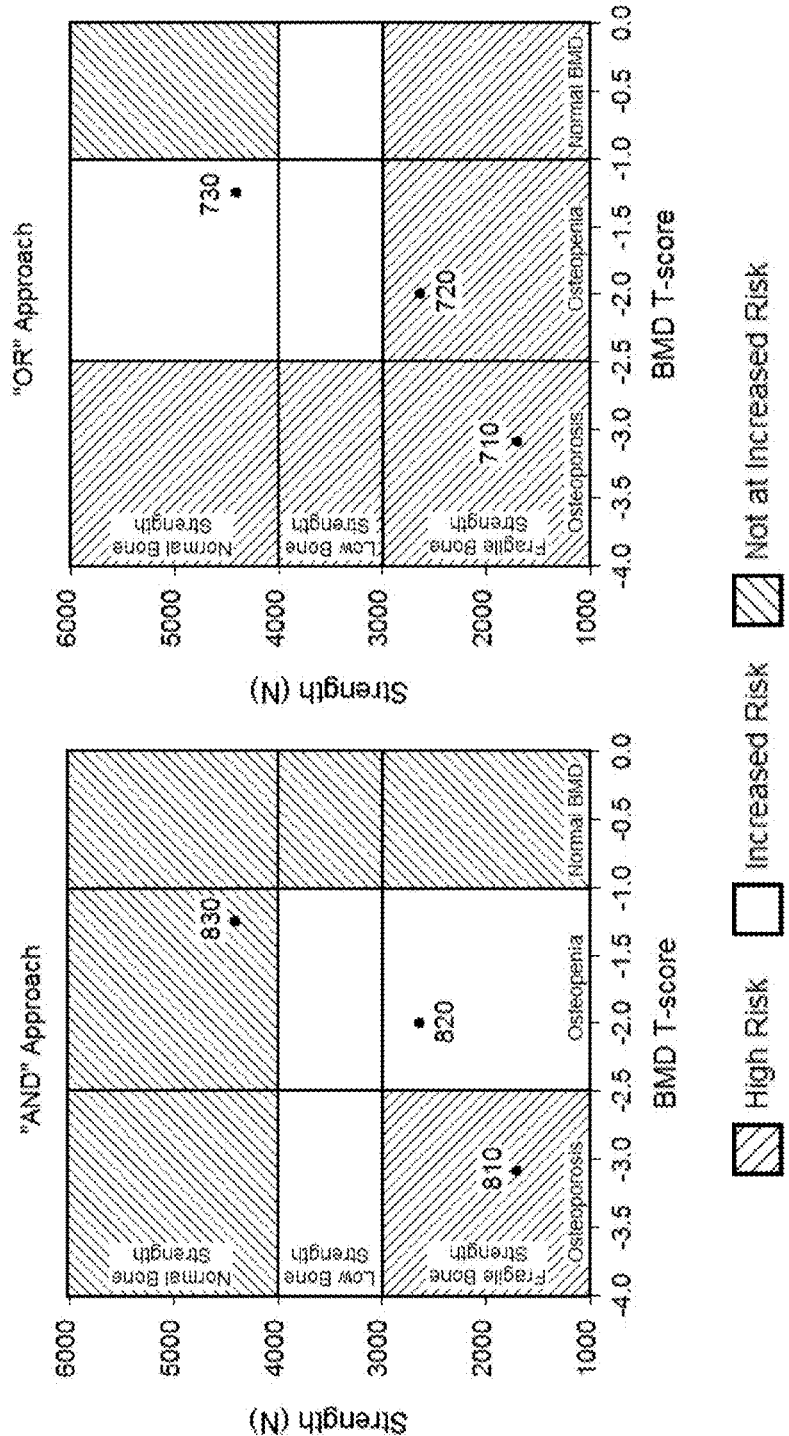
FIG. 9 illustrates two different logicals (AND, OR) for using interventional threshold values of both osteoporosis and fragile-bone-strength to determine an overall fracture risk classification.

Step 440 in system 400 determines an overall fracture risk classification based on classifications of both osteoporosis and fragile-bone-strength. One method for performing this overall fracture risk classification is depicted in FIG. 9, and such a presentation can be used in the medical report to help the physician and patient better understand the results of the test. The horizontal axis shows BMD T-scores, stratified into three classification categories: "osteoporosis" for T-score ≤2.5, "osteopenia" for −2.5<T-score <−1.0, "normal BMD" for T-score ≥1.0. The vertical axis shows strength values divided into the three statistically corresponding strength classification categories: "fragile-bone-strength" for strength ≤3000 N, "low-bone-strength" for 3000 N<strength<4000 N, and "normal-bone-strength" for strength≥4000 N. As shown in FIG. 9, the intersection of these BMD and strength classification categories creates nine distinct regions. While various different approaches to define high-risk fracture classifications are possible using these nine categories, two options are easily implemented clinically, are easy to understand, and offer unique advantages for different clinical situations. In a first "OR" approach (FIG. 9, right side), a "high risk of fracture" for the patient is defined as when the patient has either fragile-bone-strength or osteoporosis. In a second "AND" approach (FIG. 9, left side), a "high risk of fracture" is defined as the patient having both fragile-bone-strength and osteoporosis. Other fracture-risk classifications—"increased risk" and "not at increased risk"—can be defined using the OR or AND approaches, corresponding to well established BMD-based categories of osteopenia ("increased risk" of fracture) and normal BMD ("not at increased risk" of fracture).

The OR approach is less conservative than the AND approach—which to use clinically may depend on the preference of the physician or on a specific fracture type (e.g. hip vs. spine fracture), or medical condition. According to the two risk classification schemes depicted in FIG. 9, individual patient 710 would be at high risk for the OR approach and same patient 810 would also be at high risk for the AND approach; individual patient 720 would be at high risk for the OR approach but same patient 820 would only be at increased risk for the AND approach; individual patient 730 would be at increased risk for the OR approach but same patient 830 would be not at increased risk for the AND approach.

System 400 can also be applied to provide an automated screening method for patients who have had a previous CT scan containing the hip or spine. In this embodiment, a computerized system containing archived CT scans for patients, such as a PACS system, is queried for all CT scans containing the hip or spine. This query can be performed on the basis of the exam type, information that is contained within the header section of a typical DICOM-formatted CT scan, and can be performed daily, weekly, monthly or at larger time intervals. For all selected scans, the CT scan is analyzed for both BMD and bone strength. With a very high degree of automation in the software, this step can be fully automated; or, a technician can run software for these analyses; the analysis could also be performed in the cloud by transferring the images to a remote central processing site that specializes in this type of analysis of CT scans. With knowledge of the threshold values for both BMD and fragile-bone-strength, this analysis can identify patients at high risk of fracture using the AND or OR logical operators, as described above. These analyses can be performed at the hip, spine, or both sites. A medical report is thus generated and sent back to the medical practitioner and/or patient or otherwise entered into a patient's medical record and/or the PACS archiving system.

Figure 10:
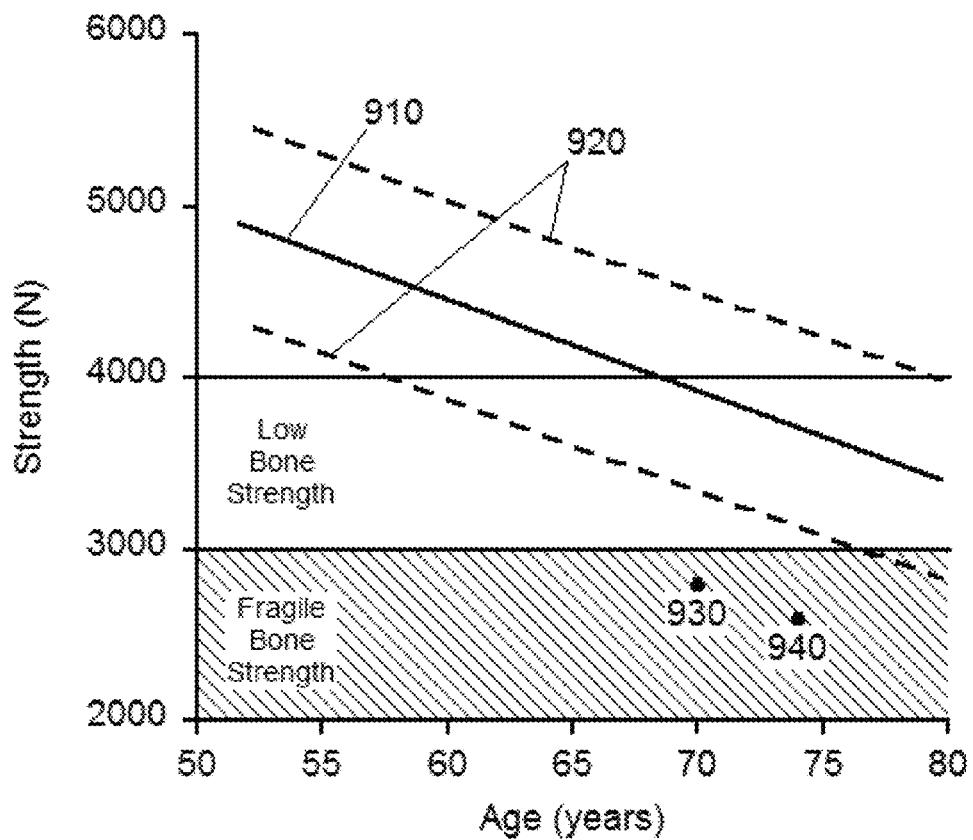
FIG. 10 illustrates a graphical representation of a patient's bone strength classification as monitored over time as it may appear in a medical report, all superimposed on a graph showing how bone strength varies with age in the population.

Specification of a predetermined interventional threshold value for fragile-bone-strength enables the generation of an improved medical report. Steps 50, 150, 250, 350 and 450 each produce a medical report with information to better assist doctors and patients with understanding the reported risk of fracture. FIG. 10 shows a graphical representation of patient's bone strength classification such as what may appear in a medical report. The plot shows age on the horizontal axis versus strength on the vertical axis. The strength axis is divided into three classification regimes by the interventional threshold values. The average relationship 910 between strength and age for a population relevant to the patient is plotted as a solid line. This population may include individuals of the same sex and race, for example. Such data can be obtained from published reports, for example, as described in Keaveny (Keaveny T M, Kopperdahl D L, Melton L J, Hoffmann P F, Amin S, Riggs B L, Khosla S: Age-dependence of femoral strength in white women and men. J Bone Miner Res, 25:994-1001, 2010), which is incorporated herein. In using published data, it is important to ensure that the strength values are numerically consistent with the strength values produced by the virtual stress test of the patient's bone. The dashed lines 920 enclose a range of strength values that are within two standard deviations of the mean strength at each age. This plot allows one to visualize a patient's bone strength relative to both average population values and to the interventional threshold values. For the age and bone strength as shown at point 930, for example, a patient would be classified as having fragile-bone-strength, and it can be seen that this patient's strength is more than two standard deviations below the average strength for similar individuals of the same age. Optionally, results from multiple reports based on CT scans acquired at different patient ages can be combined such that the progression of bone strength for the patient can be visualized in relation to the average population data and interventional threshold values. For the example in FIG. 10, the bone strength at age 74 (shown at point 940) has decreased slightly from the bone strength at age 70 (shown at point 930).

Figure 11:
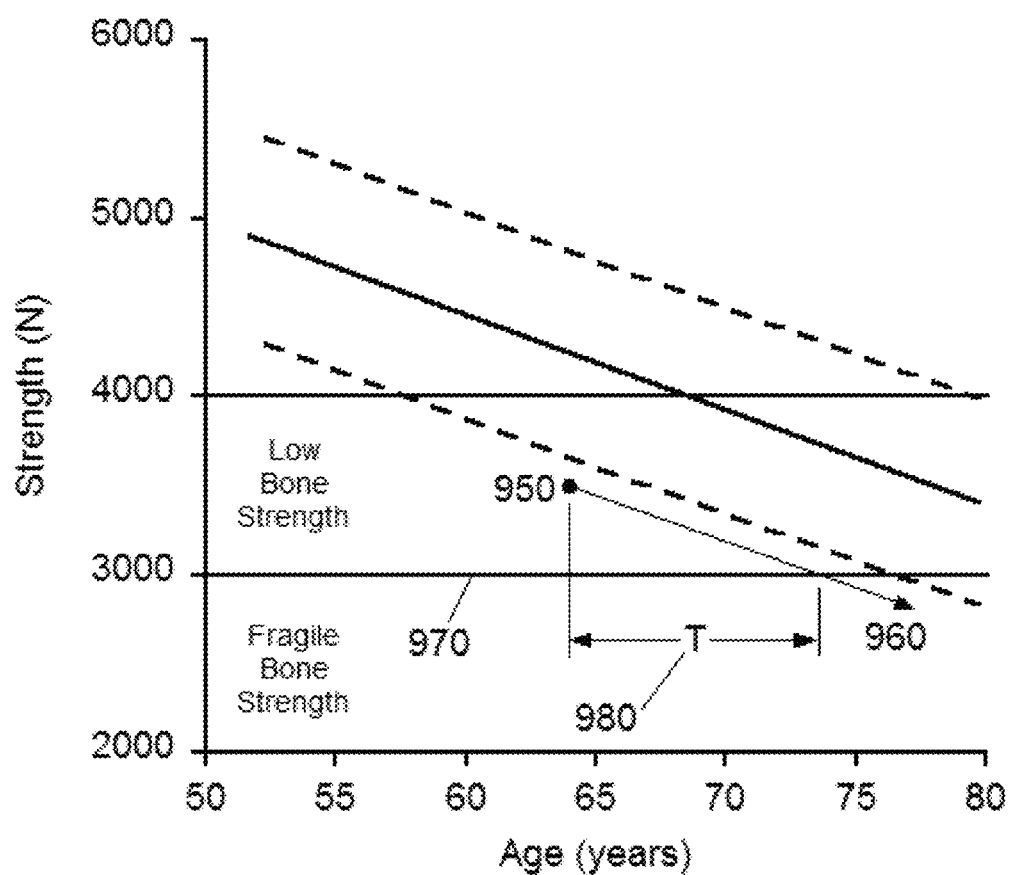
FIG. 11 illustrates a graphical representation of a patient's bone strength classification as it may appear in a medical report, all superimposed on a graph showing how bone strength varies with age on average in the population, and also showing an estimate of when that patient's bone strength might is most likely to reach the interventional threshold value for fragile-bone-strength.

In one embodiment, as depicted in FIG. 11, the report includes a calculation to help specify when an individual patient should return for a follow-up exam or begin treatment. Clinical guidelines sometimes recommend that patients get tested every two years, but many medical practitioners think this can lead to over-testing for some patients. This method addresses this issue by using the predetermined interventional threshold value for fragile-bone-strength to estimate when a follow-exam might be most appropriate, based on the relation between the patient's current bone strength and the predetermined interventional threshold value for fragile-bone-strength. FIG. 11 shows a plot similar to the plot in FIG. 10. A person with the age and bone strength depicted at point 950 has a bone strength less than an average person of the same age, and would be classified as having low-bone-strength. The average rate of bone loss for the population, depicted by the arrow 960, is used to determine the time T at which the patient's bone strength is likely to fall to the level of the interventional threshold value for fragile-bone-strength 970. This information can be written to a medical report.

Figure 12:
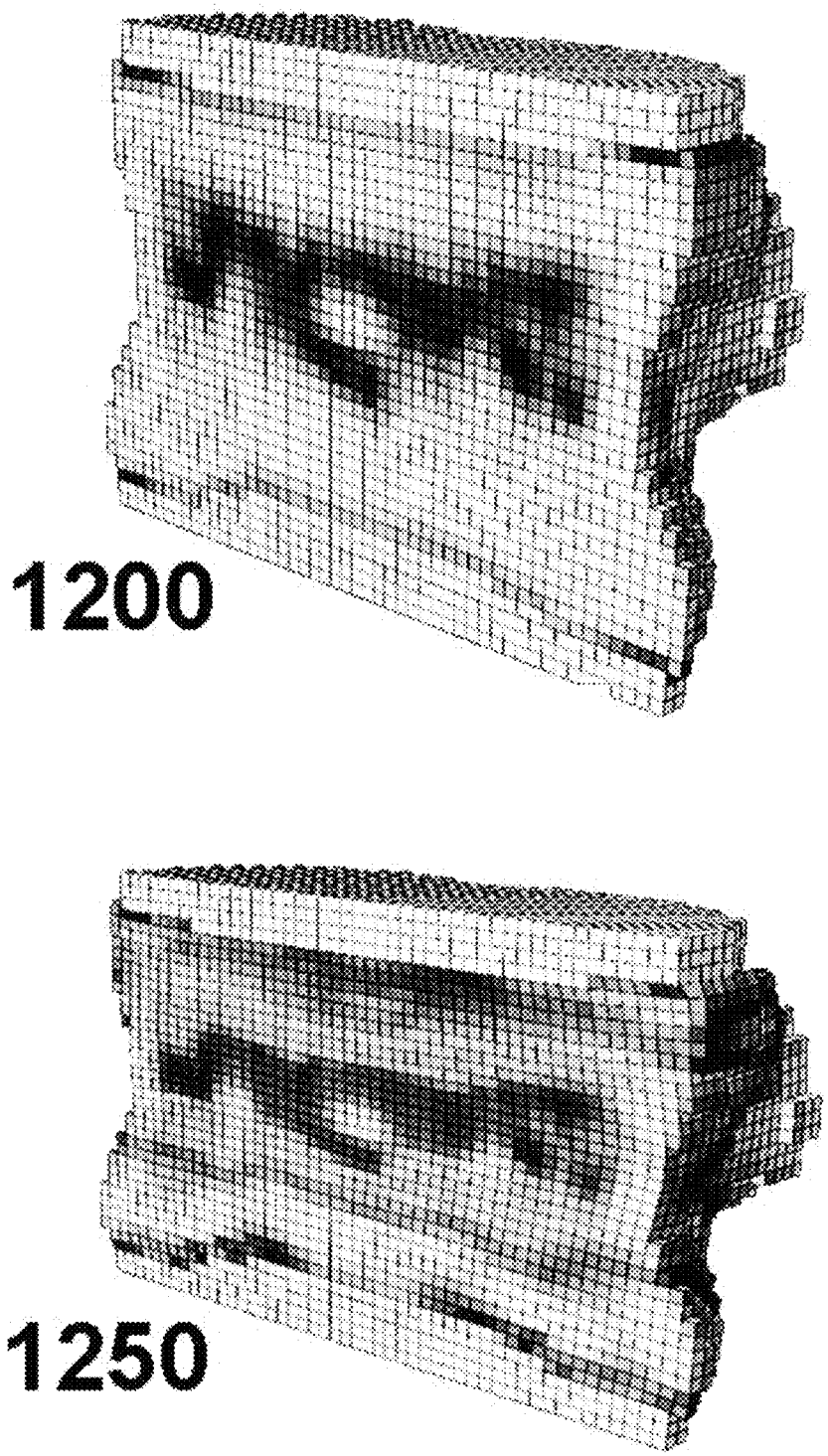
FIG. 12 illustrates two still pictures from a virtual stress test of the vertebra of a patient classified as having fragile-bone-strength, both images showing regions of damage (blackened regions) as the virtual loading progresses to increasing higher levels and the bottom image showing virtual crushing (shortening) of the bone.

Specification of a predetermined interventional threshold value for fragile-bone-strength also enables the generation of a "dynamic medical report". As noted above, the term "dynamic medical report" is used to denote a medical report that contains some form of visual information resulting from a virtual stress test of a patient's bone. For example, this report may comprise of a paper report, or equivalent electronic version, that contains one or more still images taken from the virtual stress test, as depicted in FIG. 12, typically generated using a finite element analysis of a patient's bone as it appears in a CT scan. In one embodiment, the bone is shown at an early stage of virtual loading 1200 and then again at a later stage of virtual loading, when the bone is virtually compressed 1250 in a visibly apparent manner.

In one embodiment, to render images 1200 and 1250, the displaced shape of the finite element model after virtual loading is displayed, which can be performed using any type of method for these purposes commonly used in the field of finite element analysis. A scale factor is applied to the nodal displacements to exaggerate the magnitude of the nodal displacements in order to enhance viewing of the deformed shape of the bone. Typically, a scale factor of 50-100 provides deformations can that can visually appreciated by a doctor or patient. Additionally, finite elements in the model can be colored (see darkened regions in 1200 and 1250) to indicate the location and propagation of failing bone tissue during said virtual stress test. For example, if the bone tissue is modeled constitutively as an elastic-plastic type of material, or equivalent, these colors can represent values of non-zero plastic strain, or some measure of post-yield strain or deformation of the bone, or values of a von Mises stress in excess of the assumed yield stress for any element. It should be obvious to one of ordinary skill in the art of finite element modeling of bone that a number of different approaches can be used to assign colors to failed, yielded, damaged, or fractured elements in order to convey regions of the virtual model that have failed in some way, any approach of which could be used in this embodiment.

In a further embodiment, regardless of which particular method is used to depict failed regions within the model, or how the deformed shape of the model is depicted, any such results are displayed for the loading case in which the patient's bone is virtually loaded up to a magnitude of strength (in Newtons) equal to the value of the predetermined interventional threshold value for fragile-bone-strength. For example, if the interventional threshold value for fragile-bone-strength is taken as 3,000 N, then results would be displayed for the virtual loading case in which the patient's bone is virtually loaded to a total force of 3,000 N. On the other hand, for example, if the interventional threshold value for fragile-bone-strength is taken as 4,500 N, then results would be displayed for the virtual loading case in which the patient's bone is virtually loaded to a total force of 4,500 N. In this way, this graphic display of results from the virtual stress test is displayed for virtual loading up to a load level defined by the predetermined interventional threshold value for fragile-bone-strength. Thus, by visually watching these results, a patient can easily tell if their bone "survived" the virtual stress test—the colors depicting failed tissue will only appear if the strength of the patient's bone exceeds the value of the interventional threshold value for fragile-bone-strength. If the patient can "survive" such a virtual stress test, they are not at high risk of fracture. If their bone fails during such a virtual stress test, the bone will be colored in some manner to depict such failure, and the patient should then be considered to be at a high risk of fracture and should be recommended for treatment (contingent of course on the consideration of any other relevant clinical factors by the physician). For many patients, this graphic visualization is more easily understood than is a collection of numbers and scores as presented in a more traditional style of medical report. The results can be written to a computer and viewed interactively via the web or viewed as a video or by any other means of viewing dynamic animations. A key feature of this embodiment is the integration of the interventional threshold values in these types of simulations, so that the patient is viewing their own bone loaded by force levels associated with a high risk of fracture.

In one particular embodiment, a patient's bone is virtually loaded up to the level of the interventional threshold value for fragile-bone-strength. Non-linear finite element analysis of a CT scan of the patient's bone is preferably used for such a virtual stress test, although other types of virtual stress tests could be used on other types of medical images, for example, a strength-of-materials analysis or a linear finite element analysis on a CT scan, or a finite element analysis on a DXA scan. Using the results from the virtual stress test, a deformed shape is shown, using a magnification factor for enhanced visualization. Regions of the finite element model in which the bone tissue has virtually failed are displayed in color; all other elements are not colored (or assigned some plain background color). Said coloring of the model is displayed during the visualization of the deformed shape. These results can be displayed at different stages of the virtual loading, from zero applied force up to the level of the interventional threshold value for fragile-bone-strength, to create a visual appearance of a virtual stress test in progress. Since some elements in the finite element model can fail before the overall bone is at the point of failure, colors can optionally be displayed to distinguish when the overall bone failed. For example, failed elements could be colored orange if the overall bone has not yet reached its failure or strength point, and once the bone has exceeded its strength point, any additionally failed elements could be colored red. Alternatively, failed elements may be colored continuously according to a value of plastic strain, or some other element-level result used to define failure. Alternatively, failed elements may only be colored if they exceed a limit in the underlying mechanical result, for example, rather than coloring failed elements if the plastic strain exceeds a value of zero, failed elements would be colored only when the plastic strain exceeds some specified non-zero value. In this way, minor failure of elements is not displayed. In these ways, results from the virtual stress test can be used to create dynamic virtual simulations of the bone's response to loading, for viewing by the patient, for example, using on-line viewing capabilities of some or all of the medical report on a display or monitor, or other renderer. It should be obvious to one of ordinary skill in the art that this type of visual display of the finite element model during the virtual stress test can be performed in a number of fashions within the scope of this invention and is not restricted to the specific examples described herein.

In a related embodiment, the medical report contains a result for the load case in which the patient's bone is virtually loaded to failure, and the patient's bone strength obtained from this virtual stress test to failure is visually compared in some manner to the interventional threshold value for fragile-bone-strength. One type of visual depiction is a chart of bone strength plotted in a graph on one axis versus age on the second axis, with the patient's data inserted, for example as shown in FIG. 11. Importantly, the value of the interventional threshold for fragile-bone-strength is visually included in the chart, for example, as a horizontal line in FIG. 11; or the patient's data for strength (and BMD) are presented visually on a chart displaying regions of fragile-bone-strength, such as the shaded region in FIG. 9 and FIG. 10. These types of chart are effective for some patients and benefit from the visual display of values of fragile-bone-strength, but may be difficult to understand for other patients, particularly those who do not have a firm understanding of graphs and mathematics. For such patients, other types of visual comparison may be preferred. One example is a side-by-side pair of bars or columns, the height of each bar being relatively scaled with the value of bone strength, one bar depicting the interventional threshold value for fragile-bone-strength, the other bar depicting the patient's bone strength; additional bars can be added to represent population average values, for example, an average value for the population having the same demographical profile (for example, age, sex, country, race) as the patient; additional bars can be added to show typical ranges for this population. Another example is to partially superimpose the two columns, one representing the value of the patient's bone strength from the virtual stress test and the other representing the threshold value for fragile-bone-strength. Another example is a single column, in which a portion of the height of the column is colored to represent the value of the patient's bone strength from the virtual stress test and another portion of the column is colored to represent the threshold value for fragile-bone-strength. Importantly for each example, the value of the interventional threshold value for fragile-bone-strength is visually included in the report together with the patient's bone strength value from the virtual stress testing, providing a visual comparing of the two. It should be obvious to one of ordinary skill in the art that this type of visual comparing can be performed in a number of fashions within the scope of this invention and is not restricted to the specific examples described herein.

In another embodiment, results from a virtual stress test, for virtual loading either up to the interventional threshold value for fragile-bone-strength or to failure, can also be generated for various hypothetical future scenarios in which the patient's virtual bone is virtually altered to simulate various possible treatments, including no treatment at all. The latter can be used to estimate when the patient should next be tested if they test negative for fragile-bone-strength, so that they are tested next before they are likely to have fragile-bone-strength, in time to prescribe them a preventative treatment; timing in this way also avoids follow-up testing of patients while they are unlikely to have fragile-bone-strength. This type of analysis can also be used to estimate when a patient's bone strength may improve upon treatment so it exceeds the interventional threshold value for bone strength. For example, if a patient's bone strength is estimated to be 2,600 N, and the interventional threshold value for fragile-bone-strength is 3,000 N, virtual stress tests can be performed in which the patient's bone is virtually altered to simulate treatment by one or more therapeutic agents; typical age-related bone loss can also be simulated, to estimate what the patient's bone strength will be without any treatment. One or more periods of treatment, for example, two years or five years, can be simulated for teach treatment scenario. In a medical report, results can then be visually compared with each other and against the value of the interventional threshold value for fragile-bone-strength. This comparing of the bone strength for the different treatment scenarios against the value of the interventional threshold value for fragile-bone-strength can assist the physician and patient in choosing an appropriate treatment that will most likely bring the patient's bone strength back above the interventional threshold value for fragile-bone-strength. Importantly, utilizing a value of the interventional threshold value for fragile-bone-strength facilitates clinical interpretation of such simulations.

In performing such simulations, various methods can be used to simulate treatment or aging effects in the virtual stress test. One approach is to use voxel-based statistical atlas, in which the BMD value of each voxel in a CT-based model of a patient's bone is altered on the basis of what has been measured in samples of other patients. This technique uses principles of deformable registration to perform the mapping from the statistical atlas to an individual patient's model. The patient's bone is deformed into a standardized geometry consistent with the statistical atlas, and the voxel values are altered, then the altered patient's bone is mapped back to its original geometry. See, for example, Carballido-Gamio for a description of how a statistical atlas is used to describe spatial distributions of density in a population of bones (Proximal femoral density distribution and structure in relation to age and hip fracture risk in women. Carballido-Gamio J, Hamish R, Saeed I, Streeper T, Sigurdsson S, Amin S, Atkinson E J, Therneau T M, Siggeirsdottir K, Cheng X, Melton L J 3rd, Keyak J, Gudnason V, Khosla S, Harris T B, Lang T F. J Bone Miner Res. 28:537-46, 2013), which is incorporated herein. Alternatively, average values of changes in BMD can be used to alter a patient's model, all of which can be treatment-specific. In altering a patient's model, one can use average changes from a population, or ranges of changes, for example, an upper or lower quartile, to explore most likely and less likely scenarios. It should be obvious to one of ordinary skill in the art that this type of altering of the patient's model can be performed in a number of fashions within the scope of this invention and is not restricted to the specific examples described herein.

The method disclosed in this invention may be implemented by a suitably programmed general-purpose computer system, such as by machine instructions embodied in appropriate computer readable media. For example, a computer system may function as a basic computer in implementing the present invention. The computer system includes a central processing unit (CPU), such as one of the PC microprocessors or workstations or other microprocessor or microcontroller or controller, is provided and interconnected to various other components by a system bus. An operating system runs on the CPU, and provides control and is used to coordinate the function of the various components of the system. The operating system may be one of the commercially available operating systems such as Microsoft's Windows, as well as workstation, UNIX and AIX operating systems, and the like. One or more application programs, controlled by the system, are moved into and out of a main memory RAM. These programs include the program of the present invention to be subsequently described in combination with local or wide-area network systems, such as for example, the Internet. A read only memory (ROM) is connected to the CPU via the bus and includes the Basic Input/Output System (BIOS) that controls the basic computer functions. The RAM, an I/O adapter and a communications adapter are also interconnected to the system bus. The I/O adapter may be a Small Computer System Interface (SCSI) adapter that communicates with a disk storage device. The Communications adapter interconnects the bus with an outside network enabling the data processing system to communicate with other such systems over a Local Area Network (LAN) or Wide Area Network (WAN), which includes, of course, the Internet, the WEB, intranets, extranets, and other public and private networks. The terms associated with the network are meant to be generally interchangeable and are so used in the present description of the distribution network. I/O devices are also connected to the system bus via a user interface adapter and a display adapter. A keyboard and a pointing device (e.g., a mouse) are all interconnected to the bus through the user interface adapter. The display adapter includes a frame buffer, which is a storage device that holds a representation of each pixel on a monitor or a display screen. Images may be stored in the frame buffer for display on the monitor through various components, such as a digital to analog converter and the like. By using the aforementioned I/O devices, a user is capable of inputting information to the system through the keyboard (or other input device) or mouse (or other pointing system) and receiving output information from the system via display. The system also contains a memory cache and includes a portion of a disk storage drive and a portion of RAM 125.

The system, method, and computer program product described in this application may, of course, be embodied in hardware; e.g., within or coupled to a Central Processing Unit ("CPU"), microprocessor, microcontroller, System on Chip ("SOC"), or any other programmable device. Additionally, the system, method, and computer program product may be embodied in software (e.g., computer readable code, program code, instructions and/or data disposed in any form, such as source, object or machine language) disposed, for example, in a computer usable (e.g., readable) medium configured to store the software. Such software enables the function, fabrication, modeling, simulation, description and/or testing of the apparatus and processes described herein. For example, this can be accomplished through the use of general programming languages (e.g., C, C++), GDSII databases, hardware description languages (HDL) including Verilog HDL, VHDL, AHDL (Altera HDL) and so on, or other available programs, databases, nanoprocessing, and/or circuit (i.e., schematic) capture tools. Such software can be disposed in any known computer usable medium including semiconductor, magnetic disk, optical disc (e.g., CD-ROM, DVD-ROM, etc.) and as a computer data signal embodied in a computer usable (e.g., readable) transmission medium (e.g., carrier wave or any other medium including digital, optical, or analog-based medium). As such, the software can be transmitted over communication networks including the Internet and intranets. A system, method, and computer program product embodied in software may be included in a semiconductor intellectual property core (e.g., embodied in HDL) and transformed to hardware in the production of integrated circuits. Additionally, a system, method, and computer program product as described herein may be embodied as a combination of hardware and software.

One of the preferred implementations of the present invention is as a routine in an operating system (e.g., a stored program computer including a computing device executing instructions accessed from a memory) made up of programming steps or instructions resident in a memory of a computing system as well known, during computer operations. Until required by the computer system, the program instructions may be stored in another readable medium, e.g. in a disk drive, or in a removable memory, such as an optical disk for use in a CD ROM computer input or in a floppy disk for use in a floppy disk drive computer input. Further, the program instructions may be stored in the memory of another computer prior to use in the system of the present invention and transmitted over a LAN or a WAN, such as the Internet, when required by the user of the present invention. One skilled in the art should appreciate that the processes controlling the present invention are capable of being distributed in the form of computer readable media in a variety of forms.

Any suitable programming language can be used to implement the routines of the present invention including C, C++, Java, assembly language, etc. Different programming techniques can be employed such as procedural or object oriented. The routines can execute on a single processing device or multiple processors. Although the steps, operations or computations may be presented in a specific order, this order may be changed in different embodiments. In some embodiments, multiple steps shown as sequential in this specification can be performed at the same time. The sequence of operations described herein can be interrupted, suspended, or otherwise controlled by another process, such as an operating system, kernel, and the like. The routines can operate in an operating system environment or as stand-alone routines occupying all, or a substantial part, of the system processing.

In the description herein, numerous specific details are provided, such as examples of components and/or methods, to provide a thorough understanding of embodiments of the present invention. One skilled in the relevant art will recognize, however, that embodiments of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

A "computer-readable medium" for purposes of embodiments of the present invention may be any medium that can contain, store, communicate, propagate, or transport the program for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory.

A "processor" or "process" includes any human, hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

Embodiments of the invention may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of the present invention can be achieved by any means as is known in the art. Distributed, or networked systems, components and circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope of the present invention to implement a program or code that can be stored in a machine-readable medium to permit a computer to perform any of the methods described above.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A computer-implemented method specifying an interventional threshold value of a bone strength parameter of a population data set for a plurality of subjects, each of the subjects including a bone portion, the interventional threshold value providing an indication of a fragile-bone-strength condition, comprising:
   deriving, using a finite element analysis, a bone strength value for the bone strength parameter for each subject in the plurality of subjects;
   receiving a bone mineral density (BMD) value for each subject of the plurality of subjects;
   pairing, for each particular subject in the plurality of subjects, said bone strength value and said BMD value to produce a set of paired measurements of bone strength and BMD for the plurality of subjects; and
   specifying the value for the bone strength interventional threshold responsive to an established BMD interventional threshold value for osteoporosis and a statistical correspondence of said set of paired measurements.

2. The method of claim 1 wherein said finite element analysis includes a finite element analysis of a computed tomography (CT) image of the bone portion of each said subject.

3. The method of claim 1 wherein said BMD value receiving includes measuring said BMD value from a CT scan of the bone portion.

4. The method of claim 1 wherein the interventional threshold value for the fragile-bone-strength condition includes one or more values selected from the group consisting of a vertebral strength for women of 4,500 N, a vertebral strength for men of 6,500 N, a femoral fall strength for women of 3,000 N, a femoral fall strength for men of 3,500 N, and combinations thereof.

5. The method of claim 1 wherein said bone strength parameter includes one or more parameters selected from the group consisting of a strength, a stiffness, an energy, a load-to-strength ratio, a safety factor, a factor of safety, an amount of damaged tissue, a force, a moment, a bending moment, a torsion, a fatigue strength, an endurance limit, a stress, a strain, a strain energy density, a deformation, and combinations thereof.

6. The method of claim 1 wherein the interventional threshold value for the fragile-bone-strength condition includes a value that is within ±20% of a statistically prescribed value corresponding to an established BMD interventional threshold value for osteoporosis responsive to said statistical correspondence of said set of paired measurements of bone strength and BMD.

7. The method of claim 1 wherein the interventional threshold value for the fragile-bone-strength condition includes a value that is within a range of statistically prescribed values corresponding to a range of ±0.5 T-score units of an established BMD T-score interventional threshold value for osteoporosis responsive to said statistical correspondence of said set of paired measurements of bone strength and BMD.

8. The method of claim 1 wherein the interventional threshold value for the fragile-bone-strength condition includes a value that is within a range of statistically prescribed values corresponding to a range of ±15 mg/cm$^3$ of an established BMD interventional threshold value for osteoporosis responsive to said statistical correspondence of said set of paired measurements of bone strength and BMD.

9. A non-transitory computer readable storage medium storing a program therein, for execution by a processor to generate a classification of a fragile-bone-strength condition for a patient by performing the method of:
  deriving, using a finite element analysis, a bone strength value of a bone strength parameter for a bone portion of the patient;
  receiving a predetermined interventional threshold value for the fragile-bone-strength condition for said bone strength parameter;
  classifying the patient for the fragile-bone-strength condition, which produces a fragile-bone-strength classification responsive to a processor-implemented comparison of said bone strength value and said predetermined interventional threshold value.

* * * * *

UNITED STATES PATENT AND TRADEMARK OFFICE
CERTIFICATE OF CORRECTION

PATENT NO. : 9,848,818 B1  
APPLICATION NO. : 14/455867  
DATED : December 26, 2017  
INVENTOR(S) : David L. Kopperdahl et al.

Page 1 of 1

It is certified that error appears in the above-identified patent and that said Letters Patent is hereby corrected as shown below:

In the Specification

In Column 1, Line 10, add:
STATEMENT REGARDING FEDERALLY SPONSORED RESEARCH OR DEVELOPMENT
This invention was made with government support under AR052234 awarded by National Institute of Arthritis and Musculoskeletal and Skin Diseases. The government has certain rights in the invention.

Signed and Sealed this
Twenty-second Day of May, 2018

Andrei Iancu
*Director of the United States Patent and Trademark Office*